United States Patent [19]

Ichikawa et al.

[11] Patent Number: 5,043,142

[45] Date of Patent: Aug. 27, 1991

[54] ALPHA-HYDROPEROXYISOPROPYLPHE-NYL COMPOUNDS AND PROCESS FOR PREPARING THE SAME

[75] Inventors: Syuji Ichikawa; Katsuya Fujii; Takeo Nomura, all of Tokyo, Japan

[73] Assignee: Terumo Kabushiki Kaisha, Tokyo, Japan

[21] Appl. No.: 350,707

[22] PCT Filed: Oct. 29, 1987

[86] PCT No.: PCT/JP87/00831

§ 371 Date: Nov. 17, 1989

§ 102(e) Date: Nov. 17, 1989

[87] PCT Pub. No.: WO88/03134

PCT Pub. Date: May 5, 1988

[30] Foreign Application Priority Data

| Oct. 30, 1986 | [JP] | Japan | 61-256843 |
| Oct. 30, 1986 | [JP] | Japan | 61-256844 |
| Oct. 30, 1986 | [JP] | Japan | 61-256845 |
| Oct. 30, 1986 | [JP] | Japan | 61-256846 |
| May 1, 1987 | [JP] | Japan | 62-108590 |
| May 1, 1987 | [JP] | Japan | 62-108592 |
| Jun. 2, 1987 | [JP] | Japan | 62-137633 |
| Jun. 2, 1987 | [JP] | Japan | 62-137634 |
| Jun. 2, 1987 | [JP] | Japan | 62-137635 |
| Jun. 2, 1987 | [JP] | Japan | 62-137636 |

[51] Int. Cl.$^5$ .......................... C01N 21/18
[52] U.S. Cl. ................ 422/56; 436/135; 436/166; 436/169; 436/904; 568/560; 568/563; 568/564
[58] Field of Search ............ 422/56; 436/66, 135, 436/166, 169, 904; 435/28; 568/563, 564, 560

[56] References Cited

U.S. PATENT DOCUMENTS 4,326,088   5/1982   Braus ............................. 568/563

*Primary Examiner*—Robert J. Warden
*Assistant Examiner*—Laura E. Collins
*Attorney, Agent, or Firm*—Burns, Doane, Swecker & Mathis

[57] ABSTRACT

α-Hydroperoxyisopropylphenyl compounds are useful as an organic hydroxyperoxide content in test compositions for the measurement of peroxide-active substances and are effectively utilized for detecting peroxide-active substances such as blood or hemoglobin (occult blood).

Test devices for the detection of occult blood are constituted of a carrier in which organic hydroperoxide, coloration indicator, buffering agent, wetting agent, activating agent and stabilizer are impregnated. If hemoglobin is present in a specimen, the organic hydroperoxide is activated to produce nascent oxygen with which the indicator is oxidized and develops color. Although 2,5-dimethylhexane-2,5-dihydroperoxide and cumene hydroperoxide have been employed as the organic hydroperoxide, they are disadvantageous in remarkable reduction of the detective sensitivity due to lack of the stability with elapse of time, pseudonegative judgement when vitamin C is contained in urine specimen, reduction of capacity in the multi-item test pieces for the detection of urinary components caused by discoloration of the adjacent test pieces, low coloration sensitivity, etc.

The compounds of the present invention are improved in the above-mentioned defects.

As typical examples of the α-hydroperoxy-isopropylphenyl compounds according to the invention are mentioned 4-(2,4,7-trioxaoctyl) cumene hydroperoxide, 4-(α-operoxyisopropyl)benzyl benzyl ether, 4-octyl cumene -hydroperoxyisopropyl)benzyl benzyl ether, 4-octyl cumene hydroperoxide, bis[4-(α-hydroperoxyisopropyl)benzyl]ether, N,N-dimethyl-]4-(α-hydroperoxyisopropyl)benzene]-sulfoamide and the like.

9 Claims, No Drawings

ALPHA-HYDROPEROXYISOPROPYLPHENYL COMPOUNDS AND PROCESS FOR PREPARING THE SAME

TECHNICAL FIELD

The present invention relates to α-hydroperoxyisopropylphenyl compounds and a process for preparing the same.

Furthermore, the invention is concerned with test compositions for the measurement of peroxide-active substances using as organic hydroperoxide the above-mentioned α-hydroperoxyisopropylphenyl compounds and test devices carrying said compositions.

The α-hydroperoxyisopropylphenyl compounds and the compositions or test devices containing the same are effectively utilized for detecting peroxide-active substances such as blood or hemoglobin.

It may be presumed that if blood or hemoglobin is contained in urine, feces or vomit, certain disease such as inflammation or ulcer progresses in the urinary organs or the digestive system such as the kidneys, the stomach or the intestines. Therefore, in order to promptly diagnose and treat such disease correct detection of blood or hemoglobin (occult blood) in urine, feces or vomit as mentioned above is important. The α-hydroperoxyisopropylphenyl compounds of the invention are favorably used as a reagent for the examination of such occult blood.

BACKGROUND ART

Test devices for the detection of occult blood are constituted of a carrier in which organic hydroperoxide, coloration indicator, buffering agent, wetting agent, activating agent and stabilizer are impregnated. If hemoglobin is present in a specimen, the organic hydroperoxide is activated to produce nascent oxygen with which the indicator is oxidized and develops color. As the organic hydroperoxide are known 2,5-dimethylhexane-2,5-dihydroperoxide and cumene hydroperoxide. Whereas these peroxides are in practical use, they are disadvantageous in remarkably reducing of the detective sensitivity due to lack of stability with elapse of time, pseudonegative judgement when vitamin C is contained in the urine specimen, reduction of capacity in the multi-item test pieces for the detection of urinary components caused by discoloration of the adjacent test pieces, low coloration sensitivity, etc. Compounds in which the benzene ring of cumene hydroperoxide is provided with a substituent such as a $C_{1-6}$ alkyl group, Cl, Br, I, $NO_2$ or carboxyl group have recently been proposed as the hydroperoxide with which these disadvantages are improved (Japanese Patent LOP Publication No. 190663/1984). Although the peroxides represent considerable improvement over the known compounds, the stability with elapse of time is not yet satisfactory.

DISCLOSURE OF THE INVENTION

First, it is an object of the invention to provide peroxides without the above-mentioned disadvantages and a process for preparing the same.

Second, another object of the invention is to provide test compositions for the measurement of peroxide-active substances without the above-mentioned disadvantages and test devices carrying the same.

These objects are achieved by the present invention as set forth below.

(1) An α-hydroxyperoxyisopropylphenyl compound having the general formula (I) or (II)

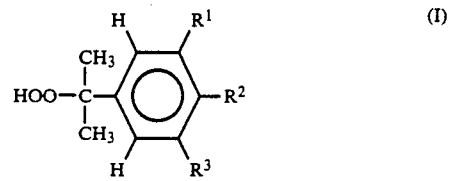

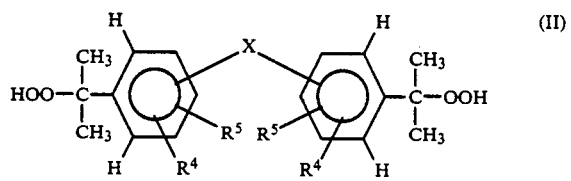

wherein $R^1$, $R^2$ and $R^3$ are the same or different and respectively represent hydrogen atom, a lower alkyl group, a halogen atom, carboxyl group, nitro group or a straight- or branched-chain oxygen-containing alkyl group having one or more ether bonds in the chain or a monovalent organic group containing sulfur atom provided that at least one of $R^1$, $R^2$ and $R^3$ represents the above-mentioned straight- or branched-chain oxygen-containing alkyl group or a monovalent organic group containing sulfur atom; X represents a straight- or branched-chain alkylene group which may contain ether bond and/or phenylene group in the chain or a divalent organic group containing sulfur atom and $R^4$ and $R^5$ are the same or different and respectively represent hydrogen atom, a lower alkyl group, a halogen atom, carboxyl group or nitro group.

(2) A compound of the formula (I) according to item 1 wherein the oxygen-containing alkyl group in $R^1$-$R^3$ is a group having 2-100 carbon atoms.

(3) A compound of the formula (I) according to item 1 wherein the oxygen-containing alkyl group in $R^1$-$R^3$ is an alkyl group represented by the formula given below.

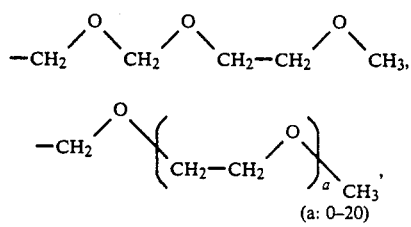

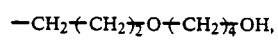

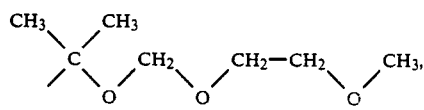

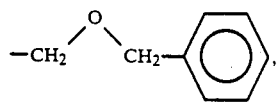

-continued

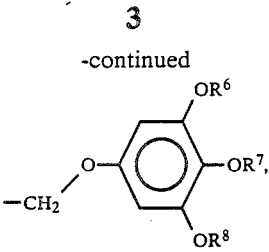

R[7]-R[8] being the same or different and respectively representing hydrogen atom or a lower alkyl group, or

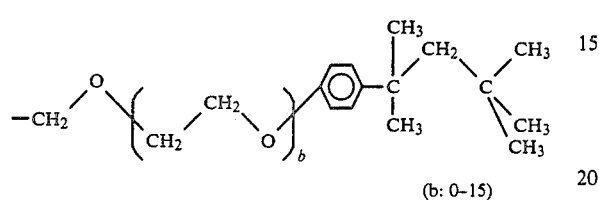

(b: 0-15)

(4) A compound of the formula (I) according to item 1 wherein the organic group in R[1]-R[3] is a sulfonyl group represented by the formula given below.

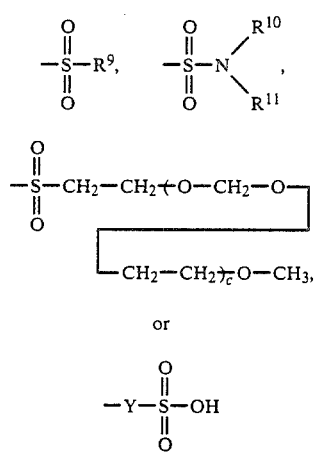

in which R[9] represents a straight- or branched-chain alkyl group, R[10] and R[11] are the same or different and respectively represent a straight- or branched-chain alkyl group or, together with nitrogen atom with which they are bonded, represent a five- or six-membered heterocyclic group which may additionally have oxygen atom, sulfur atom or nitrogen atom in the ring, Y represents a straight- or branched-chain alkylene group and C represents an integer from 0 to 5.

(5) A compound of the general formula (II) according to item 1 wherein the alkylene group in X is a group having 2–100 carbon atoms.

(6) A compound of the general formula (II) according to item 1 wherein the alkylene group in X is an alkylene group represented by the formula given below.

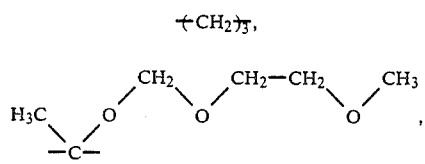

-continued

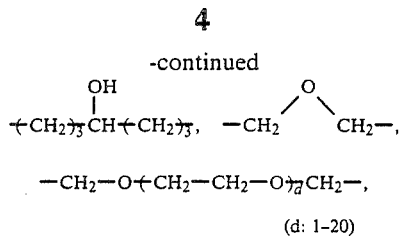

(d: 1-20)

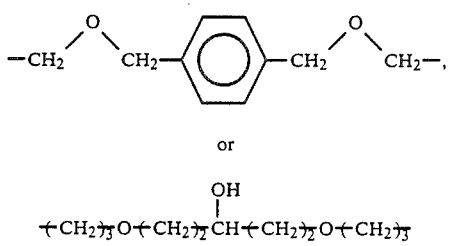

(e: 1-20)

or

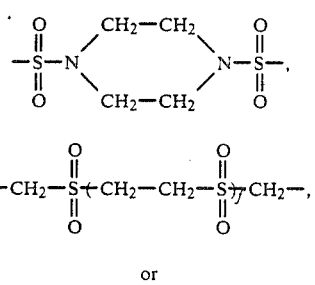

(7) a compound of the formula (II) according to item 1 wherein the organic group in X is represented by the formula given below.

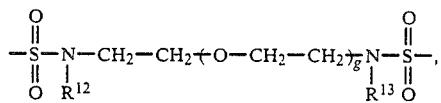

or

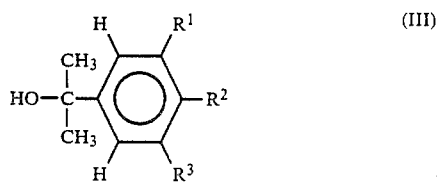

in which f and g respectively represent an integer from 0 to 5 and each of R[12] and R[13] represents a straight- or branched-chain alkyl group.

(8) A process for preparing α-hydroperoxyisopropylphenyl compounds having the general formula (I) or (II) according to item 1 which comprises oxidizing with an aqueous solution of hydrogen peroxide an α-hydroxyisopropylphenyl compound having the general formula (II) or (IV)

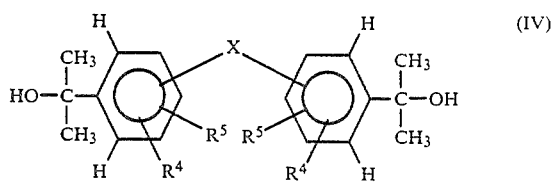

wherein $R^1$-$R^5$ and X respectively have the same meanings as defined in item 1.

(9) A test composition for the measurement of peroxide-active substances comprising an α-hydroperoxyisopropylphenyl compound having the general formula (I) or (II) according to item 1 and an oxidation coloration indicator.

(10) A composition according to item 9 wherein the oxidation coloration indicator is orthotolidine, benzidine or leucomalachite green.

(11) A test device for the measurement of peroxide-active substances comprising a carrier on which a composition containing an α-hydroperoxyisopropylphenyl compound having the general formula (I) or (II) according to item 1 and an oxidation coloration indicator is carried.

(12) A test device according to item 11 wherein the carrier is non-woven cloth made of filter paper, glass fibers or a plastic material.

In the above-mentioned formula (I), as described above, $R^1$, $R^2$ and $R^3$ are the same or different and respectively represent hydrogen atom, a lower alkyl group, a halogen atom, carboxyl group, nitro group or a straight- or branched-chain oxygen-containing alkyl group containing one or more ether bonds in the chain or a monovalent organic group containing sulfur atom provided that at least one of $R^1$, $R^2$ and $R^3$ represents the oxygen-containing alkyl group or the organic group. The oxygen-containing alkyl group may be either in straight chain or in branched chain but is required to contain one or more ether bonds in the chain. Number of the carbon atoms in the alkyl group is 2-100, preferably 2-50, although it is not particularly limited. Number of the ethers present in the oxygen-containing alkyl group is preferably 1 - 7, although there is no limitation to it so far as it is one or more. Said alkyl group may further be substituted with those substituents which will not interfere with coloration of the above-mentioned coloration indicator, for example, halogen atoms (Cl, Br, I), nitro group, hydroxyl group, sulfone group, carboxyl group, amide group, phenyl group, substituted phenyl group, etc. Preferred examples of such alkyl group are:

2,4,7-Trioxaoctyl,
2,5,8,11,14,16,19-Heptaoxaeicosanyl,
Methyl-polyethylene glycol-methyl

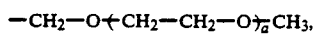

(a: 0-20)

8-Hydroxy-4-oxaoctyl,
1,1-Dimethyl-2,4,7-trioxaoctyl,
2-Oxa-3-phenylpropyl,
(Substituted)phenoxymethyl, and
1,1,3,3-Tetramethylbutyl-polyethylene glycol-methyl

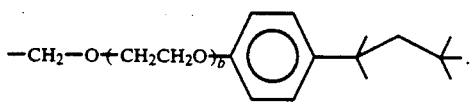

(b: 0-15)

It is desirable that the monovalent organic group containing sulfur atom contains sulfonyl group

As preferred examples of said group are mentioned groups having the formula given below.

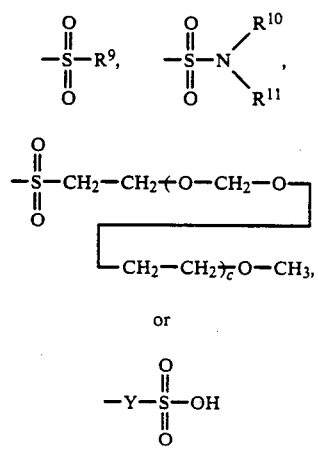

or $$-Y-\overset{O}{\underset{O}{\overset{\|}{S}}}-OH$$

$R^9$ in the above-mentioned formula is a straight- or branched-chain alkyl group containing preferably 1-8 carbon atoms, examples of which include methyl, ethyl, n-propyl, i-propyl, n-butyl, i-butyl, n-pentyl, n-hexyl, n-heptyl, n-octyl and the like.

$R^{10}$ and $R^{11}$ are the same or different and respectively represent a straight- or branched-chain alkyl group containing preferably 1-4 carbon atoms, examples of which include methyl, ethyl, n-propyl, i-propyl, n-butyl and i-butyl.

Alternatively, $R^{10}$ and $R^{11}$, together with the nitrogen atom with which they are bonded, represent a 5- or 6-membered heterocyclic group, examples of which include morpholyl, piperazyl, piperidyl and the like.

Y is an alkylene group containing preferably 1-4 carbon atoms which include, for example, methylene, ethylene, trimethylene, propylene or n-butylene.

c is an integer of preferably 1 or 2.

As especially preferred examples of the monovalent organic group containing sulfur atom are mentioned:

n-Butylsulfonyl

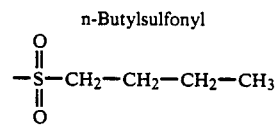

Dimethylaminosulfonyl

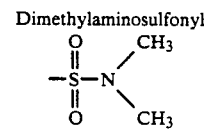

2-[(2-Methoxyethoxy)methoxy]ethylsulfonyl

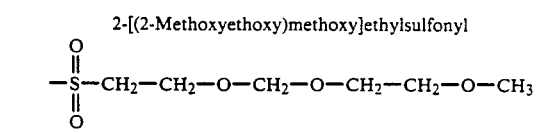

N-Morpholinesulfonyl

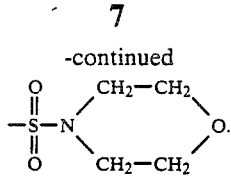

In the above-mentioned formula (II) X represents an alkylene group which may optionally contain ether bond and/or phenylene group in the chain or it represents a divalent organic group containing sulfur atom.

The alkylene group may be either in straight chain or in branched chain and contain in the chain one or more, preferably 1-7 ether bonds. Moreover, said alkylene group may contain phenylene group in the chain. In addition, said alkylene group may be substituted with those substituents which will not interfere with color development of the coloration indicator mentioned above, for example, halogen atoms (Cl, Br, I), nitro group, hydroxyl group, sulfone group, carboxyl group, amide group, phenyl group, substituted phenyl group and the like.

As preferred examples of the above-mentioned alkylene group are mentioned:
Trimethylene,
2,2-(3,5,8-Trioxa)nonanylene,
1,7-(4-Hydroxy)heptanylene,
1,3-(2-Oxa)propylene,
1,12-(2,5,8,11-Tetraoxa)decanylene,
1,21-(2,5,8,11,14,17,20-Heptaoxa)heneicosanylene,
Polyethylene glycolyl (mean value for the degree of polymerization 13),
1,14-(2,13-Dioxa)tetradecanylene

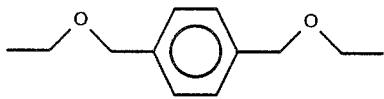

1,4-Bis[1-(2-oxa-3-propylene)]phenyl,
1,13-(7-Hydroxy-4,10-dioxa)tridecanylene,
1,6-(2,5-Dioxa)heptanylene and the like.

As preferred examples of the divalent organic group containing sulfur atom in the chain are mentioned groups having the formula set forth below.

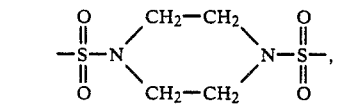

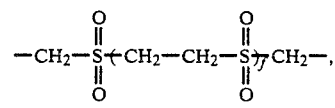

or

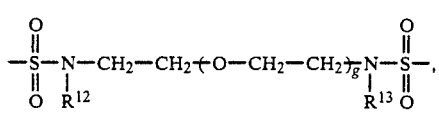

In the above formulae f and g are respectively an integer from 0 to 5, preferably from 0 to 2. Each of $R^{12}$ and $R^{13}$ is a straight- or branched-chain alkyl group having preferably 1-4 carbon atoms, methyl, ethyl or n-propyl being particularly preferable.

As especially preferred examples of the above-mentioned divalent organic group containing sulfur atom are mentioned:

N,N'-Piperazine disulfonyl

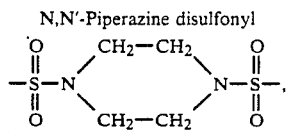

Sulfonyldimethylene

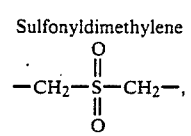

Methylenesulfonylethylenesulfonylethylenesulfonylmethylene

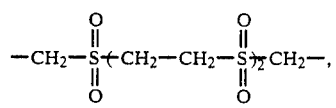

Sulfonyl-N-methylaminoethoxyethyl-N-methylaminosulfonyl

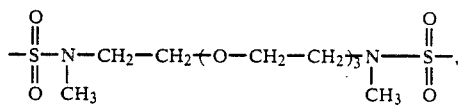

Sulfonyl-N-methylaminoethoxyethoxyethoxyethyl-N-methylaminosulfonyl

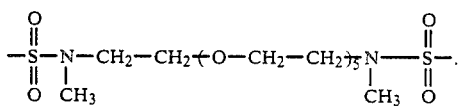

As typical compounds of the α-hydroperoxyisopropylphenyl compounds according to the invention are mentioned:
4-(2,4,7-Trioxaoctyl)cumene hydroperoxide,
4-(2,5,8,11,14,16,19-Heptaoxaeicosanyl)cumene hydroperoxide,
Polyethylene glycol 4-(α-hydroperoxyisopropyl)-benzylmethyl ether,
4-(8-Hydroxy-4-oxaoctyl)cumene hydroperoxide,
3-(1,1-Dimethyl-2,4,7-trioxaoctyl)cumene hydroperoxide,
4-(α-Hydroperoxyisopropyl)benzyl benzyl ether,
4-(α-Hydroperoxyisopropyl)benzyl 4-nitrobenzyl
4-(α-Hydroperoxyisopropyl)benzyl 3,4,5-trimethoxyphenyl ether,
Polyethylene glycol 4-(α-hydroperoxyisopropyl)benzyl 4-(1,1,3,3-tetramethylbutyl)phenyl ether,
3,4-Bis(2,5,8,11,14-pentaoxapentadecanyl)cumene hydroperoxide,
3,4,5-Tris(2-oxa-3-phenylpropyl)cumene hydroperoxide,
1-Chloro-4-(α-hydroperoxyisopropyl)-2-(2-methoxyethoxymethoxymethyl)benzene,
4-(α-Hydroperoxyisopropyl)-2-methylbenzyl benzyl ether,
4-(α-Hydroperoxyisopropyl)-2,6-dichlorobenzyl benzyl ether,
1,3-Bis[4-(α-hydroperoxyisopropyl)phenyl]propane, 2,2-Bis[4-(α-hydroperoxyisopropyl)phenyl]-3,5,8-trioxanonane,
1,7-Bis[4-(α-hydroperoxyisopropyl)phenyl]-4-hydroxyheptane,
4-(α-Hydroperoxyisopropyl)benzyl ether
20    1,12-Bis[4-(α-hydroperoxyisopropyl)phenyl]-2,5,8,11-tetraoxadodecane,
1,21-Bis[4-(α-hydroperoxyisopropyl)phenyl]-2,5,8,11,14,17,20-heptaoxaheneicosane,
Polyethylene glycol bis[4-(α-hydroperoxyisopropyl)benzyl]ether,
1,14-Bis[4-(α-hydroperoxyisopropyl)phenyl]-2,13-dioxatetradecane,
1,4-Bis[3-[4-(α-hydroperoxyisopropyl)phenyl]-2-oxapropyl]benzene
1,13-Bis[4-(α-hydroperoxyisopropyl)phenyl]-7-hydroxy-4,10-dioxatridecane,
1,6-Bis[3-(α-hydroperoxyisopropyl)phenyl]-2,5-dioxaheptane,
Bis[2-chloro-4-(α-hydroperoxyisopropyl)benzyl]ether,
1,9-Bis[2-chloro-4-(α-hydroperoxyisopropyl)-phenyl]-2,5,8-trioxanonane,
1,21-Bis[4-(α-hydroperoxyisopropyl)-2-methylphenyl]-2,5,8,11,14,17,20-heptaoxaheneicosane,
1-[4-(α-Hydroperoxyisopropyl)benzenesulfonyl]-butane,
N,N-Dimethyl-[4-(α-hydroperoxyisopropyl)-benzene]-sulfoamide,
1-[4-(α-Hydroperoxyisopropyl)benzene]sulfonyl-3,5,8-trioxanonane,
N-[4-(α-Hydroperoxyisopropyl)benzenesulfonyl]-morpholine,
N,N'-Bis[4-(α-hydroperoxyisopropyl)benzenesulfonyl]-piperazine,
Bis[4-(α-hydroperoxyisopropyl)benzyl]sulfone,
2-[2-[α-[4-(α-Hydroperoxyisopropyl)toluene]-sulfonyl]ethanesulfonyl]ethanesulfonylmethyl-4-(α-Hydroperoxyisopropyl)benzene,
N,N'-Bis[4-(α-hydroperoxyisopropyl)benzenesulfonyl]-N,N'-dimethyl-3,6,9-trioxaundecane-1,11-diamine, and
N,N'-Bis[4-(α-hydroperoxyisopropyl)-benzenesulfonyl]-N,N'-dimethyl-3,6,9,12,15-pentaoxaheptadecane-1,17-diamine.

The α-hydroperoxyisopropylphenyl compounds represented by the above-mentioned formula (I) or (II) according to the invention are novel compounds and are prepared by oxidizing under acid conditions an α-hydroperoxyisopropylphenyl compound represented by the above-mentioned formula (III) or (IV) in an aqueous solution of hydrogen peroxide. Preferably, the α-hydroperoxyisopropylphenyl compound (III) or (IV) is dissolved in an appropriate organic solvent such as ether, and to the solution are added 30% or 50% aqueous solution of hydrogen peroxide and a small amount of a mineral acid such as sulfuric or hydrochloric acid. The mixture is reacted at room temperature for ten and odd hours. After completion of the reaction, the desired product is isolated from the reaction product in a conventional manner. For example, water is added to the reaction mixture, which is then extracted with an appropriate organic solvent such as ethyl acetate. The solvent is distilled off from the extract, and the residue is purified by such means as column chromatography to obtain the desired product.

The α-hydroperoxyisopropylphenyl compounds (III) or (IV) are produced by reacting a phenyl compound represented by the general formula (V) or (VI)

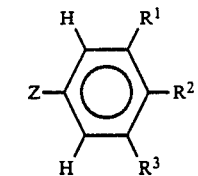

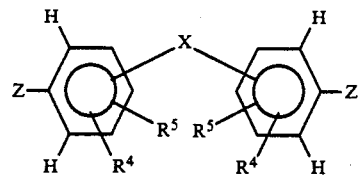

wherein $R^1$–$R^5$ and X respectively have the same meaning as defined above and Z is a halogen atom with n-butyllithium (or magnesium) and then with acetone. For example, the two compounds are reacted in an appropriate organic solvent such as, for example, tetrahydrofuran or diethyl ether at $-78°$ C. (in case of n-butyllithium) or a temperature from room temperature to refluxing condition (in case of magnesium) followed by addition of acetone to produce the compound (III) or (IV).

As described above, the α-hydroperoxyisopropylphenyl compounds (I) or (II) of the invention are used as peroxide in the measurement of peroxide-active substances, and especially useful for detecting occult blood in urine, feces and vomit.

The test devices comprise a carrier on which a composition constituted of the α-hydroperoxyisopropylphenyl compound (I) or (II) of the invention, a coloration indicator, and if needed, buffering agent, wetting agent, activating agent, stabilizer and solvent is impregnated.

As the indicator is used a so-called oxidation indicator develops color by oxidation. As examples are mentioned orthotolidine, benzidine, leucomalachite green and the like.

The buffering agent is employed for maintaining a constant pH values on the test device. Preferred agents are, for example, citrate, malonate or succinate that can maintain pH value in the range of 4–8 when the test device is soaked in a sample. The wetting agent is used in order that the sample solution will uniformly be wetted when the test device is soaked in a sample and is preferably exemplified by surface-active agents such as sodium laurylsulfate, sodium dodecylbenzenesulfonate and sodium dioctylsulfosuccinate. The activating agent is used for enhancing sensitivity of the color-developing reaction on the test device and preferably is 3-aminoquinoline, quinine, isoquinoline or the like. As the stabilizer is used a thickener for preventing elution of the test reagents from the test device, which is preferably a polymer such as polyvinyl alcohol, polyvinylpyrrolidone or polyethylene glycol, or gelatin or gum arabic. The solvent may be any of those in which a mixture of the above-mentioned reagents is readily soluble, and ethyl alcohol, acetone, benzene, toluene, chloroform and the like are advantageously employed. The carrier may be any one being neither soluble in nor reactive with the above-mentioned solvent and capable of absorbing the above-mentioned composition, a nonwoven cloth composed of filter paper, glass fibers or a plastic material being desirable.

Amounts of the α-hydroperoxyisopropylphenyl compound and other reagents used in the above-mentioned test composition and test device are not critical but appropriately determined with reference to prior art. As a matter of fact, they are selected so as to be sufficient to cause reaction with the subject peroxide-active substance and color-developing reaction.

The invention will be described below in more particular with reference to examples and test examples.

EXAMPLE 1

4-(2,4,7,-Trioxaoctyl)cumene hydroperoxide

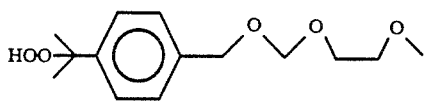

To a solution of 4.56 g (24.4 mmol) of 4-bromobenzyl alcohol in dry dichloromethane (48 ml) were added in an atmosphere of argon 3.32 ml (29.1 mmol) β-methoxyethoxymethyl chloride and 6.40 ml (36.7 mmol) of N,N-diisopropylethylamine, and the mixture was allowed to react at room temperature for 15 hours. To the resulting solution was added water followed by extraction with dichloromethane. The organic layer was washed with water and concentrated under reduced pressure. The residue thus obtained was subjected to silica gel column chromatography for separation and purification. Elution with dichloromethane yielded 6.18 g (22.5 mmol) of 4-bromo-1-(2,4,7-trioxaoctyl)benzene.

To a solution of 6.18 g (22.5 mmol) of the above-obtained compound in dry tetrahydrofuran (180 ml) was added 1.60M hexane solution of n-butyllithium in the atmosphere of argon at −78° C., and the mixture was allowed to react for 30 min. To the resulting solution was added 8.3 ml (113 mmol) of acetone, and the mixture was reacted at −78° C. for 10 min. followed by addition of saturated aqueous solution of ammonium chloride and extraction with ethyl acetate. The organic layer was washed with water and subjected to concentration under reduced pressure. The residue thus obtained was subjected to silica gel column chromatography for separation and purification. Elution with dichloromethane-methanol (25:1) yielded 3.78 g (14.9 mmol) of 1-(α-hydroxyisopropyl)-4-(2,4,7-trioxaoctyl)benzene.

To 3.78 g (14.9 mmol) of the above-obtained hydroxy compound were added 10 ml of ether, 20 ml of 30% aqueous solution of hydrogen peroxide and 0.500 ml of concentrated sulfuric acid, and the mixture was allowed to react at room temperature for 18 hours followed by addition of water and extraction with ethyl acetate. The organic layer was washed with water and concentrated under reduced pressure. The residue thus obtained was subjected to silica gel column chromatography for separation and purification. Elution with ethyl acetate-hexane (1:1) yielded 3.30 g (12.2 mmol) of 4-(2,4,7-trioxaoctyl)cumene hydroperoxide.

NMR (ppm, CDCl$_3$)
8.22(s, 1 H), 7.48–7.17(m, 4 H), 4.73(s, 2 H),
4.57(s, 2 H), 3.82–3.43(m, 4 H), 3.35(s, 3 H),
1.57(s, 6 H).
IR($\nu$cm$^{-1}$,CHCl$_3$) 3530, 3330.

EXAMPLE 2

4-(2,5,8,11,14,16,19-Heptaoxaeicosanyl)cumene hydroperoxide

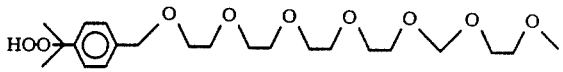

To a solution of 1.49 g (37.3 mmol) of sodium hydride contained at 60% in mineral oil in dry dimethylformamide (70 ml) was added 7.00 g (24.8 mmol) of 3,6,9,12,14,17-hexaoxaoctadeca-1-nol in an atmosphere of argon, and the mixture was allowed to react at 40°–50° C. for 30 min. To the reaction mixture was added 5.17 g (20.7 mmol) of 4-bromobenzyl bromide at room temperature for 16 hours. To the reaction mixture at 0° C. was added a saturated aqueous solution of ammonium chloride followed by extraction with ethyl acetate. The organic layer was washed with water and concentrated under reduced pressure. The residue thus obtained was subjected to silica gel column chromatography for separation and purification. Elution with dichloromethane yielded 8.03 g (17.8 mmol) of 1-bromo-4-(2,5,8,11,14,16,19-heptaoxaeicosanyl)benzene.

To a solution of 8.03 g (17.8 mmol) of the above-obtained compound in dry tetrahydrofuran (200 ml) was added 1.60M hexane solution of n-butyllithium (16.7 ml, 26.7 mmol) in the atmosphere of argon at −78° C. The mixture was allowed to react for 30 min. To the solution was added 6.50 ml (88.5 mmol) of acetone, and the mixture was reacted at −78° C. for 10 min. To the reaction mixture was added a saturated aqueous solution of ammonium chloride followed by extraction with ethyl acetate. The organic layer was washed with water and concentrated under reduced pressure. The residue thus obtained was subjected to silica gel column chromatography for separation and purification. Elution with dichloromethane-methanol(50:1) yielded 7.28 g (16.9 mmol) of 4-(2,5,8,11,14,16,19-heptaoxaeicosanyl)-1-(α-hydroxyisopropyl)benzene.

To 7.28 g (16.9 mmol) of the above-obtained hydroxy compound were added 20 ml of ether, 40 ml of 30% aqueous solution of hydrogen peroxide and 1.00 ml of concentrated sulfuric acid. The mixture was allowed to react at room temperature for 15 hours followed by addition of water and extraction with ethyl acetate. The organic layer was washed with water and concentrated under reduced pressure. The residue thus obtained was subjected to silica gel column chromatography for separation and purification. Elution with ethyl acetate-hexane (2:1) yielded 5.36 g (12.0 mmol) of 4-(2,5,8,11,14,16,19-heptaoxaeicosanyl)cumene hydroperoxide.

NMR (ppm, CDCl$_3$)
8.48(s, 1 H), 8.47–8.17(m, 4 H), 4.68(s, 2 H),
4.50(s, 2 H), 3.63 (s, 2 H), 3.35(s, 3 H), 1.57(s, 6 H) .
IR($\nu$cm$^{-1}$,CHCl$_3$) 3530, 3330.

EXAMPLE 3

Polyethylene glycol 4-(α-hydroperoxyisopropyl)benzyl methyl ether

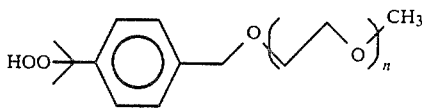

(average value for n 16)

To a solution of 1.63 g (40.8 mmol) of sodium hydride contained at 60% in mineral oil in dry dimethylformamide (60 ml) was added in an atmosphere of argon 4.94 g (6.59 mmol on average) of polyethylene glycol methyl ether with an average molecular weight of 750, and the mixture was allowed to react at 40°–50° C. for 30 min. To the reaction mixture was added 2.47 g (9.88 mmol) of 4-bromobenzyl bromide, and the mixture was allowed to react at room temperature for 16 hours. To the reaction mixture at 0° C. was added a saturated aqueous solution of ammonium chloride followed by extraction with ethyl acetate. The organic layer was washed with water and concentrated under reduced pressure. The residue thus obtained was subjected to silica gel column chromatography for separation and purification. Elution with dichloromethane-methanol (50:1) yielded 3.81 g (4.15 mmol on average) of a compound of the structure shown below.

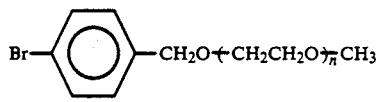

(average value for n 16)

To a solution of 3.81 g (4.15 mmol on average) of the above-obtained compound in dry tetrahydrofuran (40 ml) was added 1.60M hexane solution of n-butyllithium (3.90 ml, 6.24 mmol) in the atmosphere of argon at −78° C., and the mixture was allowed to react for 30 min. To the solution was added 2.60 ml (35.4 mmol) of acetone, and the mixture was allowed to react at −78° C. for 10 min. To the reaction mixture was added a saturated aqueous solution of ammonium chloride followed by extraction with ethyl acetate. The organic layer was washed with water and concentrated under reduced pressure. The residue thus obtained was subjected to silica gel column chromatography for separation and purification. Elution with dichloromethane-methanol (50:1) yielded 2.19 g (2.48 mmol on average) of a compound of the structure shown below.

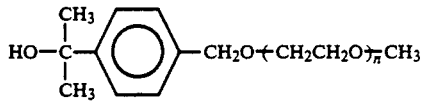

(average value for n 16)

To 2.19 g (2.48 mmol on average) of the above-obtained hydroxy compound were added 20 ml of ether, 40 ml of a 30% aqueous solution of hydrogen peroxide and 1.00 ml of concentrated sulfuric acid. The mixture was allowed to react at room temperature for 18 hours followed by addition of water and extraction with ethyl acetate. The organic layer was washed with water and concentrated under reduced pressure. The residue thus obtained was subjected to silica gel column chromatography for separation and purification. Elution with dichloromethane-methanol (25:1) yielded 1.06 g (1.18 mmol on average) of the desired product.

NMR (ppm, CDCl$_3$)

8.30(bs, 1 H), 7.47–7.10(m, 4 H), 4.50(s, 2 H), 3.63(s, 64 H), 3.33(s, 3 H), 1.48(s, 6 H).
IR($v$cm$^{-1}$,CHCl$_3$) 3530, 3330.

EXAMPLE 4

4-(8-Hydroxy-4-oxaoctyl)cumene hydroperoxide

To a solution of 1.00 g (10.2 mmol) of 1,4-butanediol in 20 ml of dry dimethylformamide were added 2.80 g (10.2 mmol) of tert-butyldiphenylsilyl chloride and 3.47 g (51.0 mmol) of imidazole in an atmosphere of argon. The mixture was allowed to react at 0° C. for 24 hours. To the solution was added water followed by extraction with dichloromethane. The organic layer was washed with water and concentrated under reduced pressure. The residue thus obtained was subjected to silica gel column chromatography for separation and purification. Elution with dichloromethane-methanol (100:1) yielded 2.17 g (6.62 mmol) of 4-(tert-butyldiphenylsiloxy)-1-butanol.

To a solution of 2.17 g (6.62 mmol) of said compound in dry pyridine (48 ml) was added 1.39 g (7.29 mmol) of p-toluenesulfonyl chloride in the atmosphere of argon. The mixture was allowed to react at room temperature for 6 hours followed by addition of water and extraction with benzene. The organic layer was washed with water and concentrated under reduced pressure. The residue thus obtained was subjected to silica gel column chromatography for separation and purification. Elution with dichloromethane-hexane (1:2) yielded 2.94 g (6.10 mmol) of 4-(tert-butyldiphenylsiloxy)-1-(p-toluenesulfoxy)butane.

Next, to a solution of 405 mg (10.1 mmol) of sodium hydride contained at 60% in mineral oil in dry dimethylformamide (20 ml) was added 1.44 g (6.70 mmol) of 3-(4-bromophenyl)-1-propanol in the atmosphere of argon, and the mixture was allowed to react at 100° C. for 30 min. To the reaction mixture was then added 2.94 g (6.10 mmol) of 4-(tert-butyldiphenylsiloxy)-1-(p-toluenesulfoxy)butane, and the mixture was reacted at 100° C. for 16 hours. To the reaction mixture at 0° C. was added a saturated aqueous solution of ammonium chloride followed by extraction with benzene. The organic layer was washed with water and then concentrated under reduced pressure. The residue thus obtained was subjected to silica gel column chromatography for separation and purification. Elution with dichloromethane-hexane (1:4) yielded 1.29 g (2.46 mmol) of 4-[8-(tert-butyldiphenylsiloxy)-4-oxaoctyl]-1-bromobenzene.

To a solution of 1.29 g (2.46 mmol) of the above-obtained compound in dry tetrahydrofuran (50 ml) was added 1.60M hexane solution of n-butyllithium (1.85 ml, 2.96 mmol) in the atmosphere of argon at −78° C., and the mixture was allowed to react for 30 min. To the solution was added 1.00 ml (13.6 mmol) of acetone, and the mixture was reacted at −78° C. for 10 min. followed by addition of saturated solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 898 mg (1.84 mmol) of 4-[8-(tert-butyldiphenylsiloxy)-4-oxaoctyl]-1-(α-hydroxyisopropyl)-benzene.

To 898 mg (1.84 mmol) of the above-obtained hydroxy compound were added 5 ml of ether, 10 ml of a 30% aqueous solution of hydrogen peroxide and 0.25 ml of concentrated sulfuric acid. The mixture was allowed to react at room temperature for 11 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:2) yielded 853 mg (1.69 mmol) of 4-[8-(tert-butyldiphenylsiloxy)-4-oxaoctyl]cumene hydroperoxide.

Next, to a solution of 853 mg (1.69 mmol) of the above-obtained compound in dry tetrahydrofuran (16 ml) was added a 1.0M tetrahydrofuran solution of tetrabutylammonium fluoride (3.40 ml, 3.40 mmol) in the atmosphere of argon, and the mixture was allowed to react at room temperature for 6 hours. To the solution was added water, and the mixture was extracted with ethyl acetate. The organic layer was washed with water and then concentrated under reduced pressure. The residue thus obtained was subjected to silica gel column chromatography for separation and purification. Elution with dichloromethane-methanol yielded 428 mg (1.52 mmol) of 4-(8-hydroxy-4-oxaoctyl)cumene hydroperoxide.

NMR (ppm, CDCl$_3$)
8 03(s, 1 H), 7.38–7.04(m, 4 H), 3.52–3.16 (m, 6 H), 2.56–2.23(m, 2 H), 2.06–1.77(m, 6 H), 1.56(s, 6 H).
IR($\nu$cm$^{-1}$,CHCl$_3$) 3610, 3530, 3400.

EXAMPLE 5

3-(1,1-Dimethyl-2,4,7-trioxaoctyl)cumene hydroperoxide

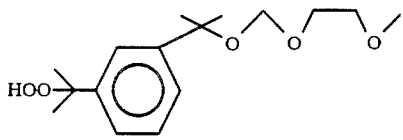

To a solution of 3.34 g (16.8 mmol) of 3'-bromoacetophenone in dry diethyl ether (68 ml) was added 1.4M diethyl ether solution of methyllithium (18.0 ml, 25.2 mmol) in an atmosphere of argon at 0° C., and the mixture was allowed to react for 30 min. To the solution was added a saturated aqueous solution of ammonium chloride, and the mixture was extracted with ethyl acetate. The organic layer was washed with water and then concentrated under reduced pressure. The residue thus obtained was subjected to silica gel column chromatography for separation and purification. Elution with dichloromethane-methanol yielded 3.47 g (16.1 mmol) of 3-(α-hydroxyisopropyl)-1-bromobenzene.

To a solution of 3.47 g (16.1 mmol) of the above-obtained compound in dry dichloromethane (35 ml) were added in the atmosphere of argon 2.20 ml (19.3 mmol) β-methoxyethoxy methyl chloride and 4.20 ml (24.1 mmol) of N,N-diisopropylethylamine, and the mixture was refluxed for 16 hours. To the solution was added water, and the mixture was extracted with dichloromethane. The organic layer was washed with water and concentrated under reduced pressure. The residue thus obtained was subjected to silica gel column chromatography for separation and purification. Elution with dichloromethane yielded 4.34 g (14.3 mmol) of 3-(1,1-dimethyl-2,4,7-trioxaoctyl)-1-bromobenzene.

To a solution of 4.34 g (14.3 mmol) of the above-obtained compound in dry tetrahydrofuran (160 ml) was added 1.60M hexane solution of n-butyllithium (13.4 ml, 21.4 mmol) in the atmosphere of argon at −78° C., and the mixture was allowed to react for 30 min. To the solution was added 5.30 ml (72.2 mmol) of acetone, and the mixture was reacted −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (50:1) yielded 3.51 g (12.4 mmol) of 3-(1,1-dimethyl-2,4,7-trioxaoctyl)-1-(α-hydroxyisopropyl)-benzene.

To 3.51 g (12.4 mmol) of the above-obtained hydroxy compound were added 20 ml of ether, 40 ml of a 30% aqueous solution of hydrogen peroxide and 1.00 ml of concentrated sulfuric acid, and the mixture was allowed to react at room temperature for 14 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 3.07 g (10.3 mmol) of 3-(1,1-dimethyl-2,4,7-trioxaoctyl)cumene hydroperoxide.

NMR (ppm, CDCl$_3$)
8.20(s, 1 H), 7.55–7.23(m, 4 H), 4.71(s, 2 H), 3.85–3.31(m, 4 H), 3.33(s, 3 H), 1.95(s, 6 H), 1.55(s, 6 H).
IR($\nu$cm$^{-1}$,CHCl$_3$) 3530, 3320.

EXAMPLE 6

4-(α-Hydroperoxyisopropyl)benzyl benzyl ether

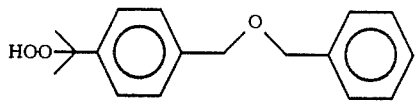

To a solution of 1.07 g (26.8 mmol) of sodium hydride contained at 60% in mineral oil in dry dimethylformamide (80 ml) was added 4.02 g (21.5 mmol) of benzyl alcohol in an atmosphere of argon, and the mixture was allowed to react at 40°–50° C. for 30 min. To the reaction mixture was then added 4.47 g (17.9 mmol) of 4-bromobenzyl bromide, and the mixture was allowed to react at room temperature for 19 hours. To the reaction mixture at 0° C. was added a saturated aqueous solution of ammonium chloride, and the mixture was extracted with ethyl acetate. The organic layer was washed with water and then concentrated under reduced pressure. The residue thus obtained was subjected to silica gel column chromatography for separation and purification. Elution with dichloromethane-hexane (1:2) yielded 4.61 g (16.6 mmol) of 4-bromophenyl benzyl ether.

To a solution of 4.61 g (16.6 mmol) of the above-obtained compound in dry tetrahydrofuran (100 ml) was added 1.21 g (49.8 mmol) of magnesium in the atmosphere of argon, and the mixture was allowed to react at room temperature for 2 hours. To the solution was added 7.50 ml (102 mmol) of acetone, and the mixture was reacted at 0° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 3.45 g (13.5 mmol) of 4-(α-hydroxyisopropyl)-benzyl benzyl ether.

To 3.45 g (13.5 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 14 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:2) yielded 3.23 g (11.9 mmol) of 4-(α-hydroperoxyisopropyl)benzyl benzyl ether.

NMR (ppm, CDCl$_3$)
8.23(bs, 1 H), 7.52–7.20(m, 9 H), 4.52(s, 4 H), 1.57(s, 6 H).
IR($v$cm$^{-1}$,CHCl$_3$) 3530, 3320.

EXAMPLE 7

4-(α-Hydroperoxyisopropyl)benzyl 4-nitrobenzyl ether

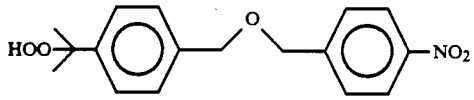

To a solution of 812 mg (20.3 mmol) of sodium hydride contained at 60% in mineral oil in dry dimethylformamide (100 ml) was added 3.01 g (16.1 mmol) of 4-bromobenzyl alcohol in the atmosphere of argon, and the mixture was allowed to react at 40°–50° C. for 30 min. followed by addition of 2.85 g (13.2 mmol) of 4-nitrobenzyl bromide. The mixture was reacted at room temperature for 17 hours. To the reaction mixture at 0° C. was added saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (1:1) yielded 2.76 g (8.57 mmol) of 4-bromobenzyl 4-nitrobenzyl ether.

To a solution of 2.76 g (8.57 mmol) of the above-mentioned compound in dry tetrahydrofuran (90 ml) at −78° C. was added 1.60M hexane solution of n-butyllithium (6.43 ml, 10.3 mmol), and the mixture was allowed to react for 30 min. To the resulting solution was added 3.20 ml (43.6 mmol) of acetone, and the mixture was allowed to react at −78° C. for 10 min. To the reaction mixture was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-methanol (50:1) yielded 1.37 g (4.55 mmol) of 4-(α-hydroxyisopropyl)benzyl 4-nitrobenzyl ether.

To 1.37 g (4.55 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 1.01 g (3.19 mmol) of 4-(α-Hydroperoxyisopropyl)benzyl 4-nitrobenzyl ether.

NMR (ppm, CDCl$_3$)
8.23(s, 1 H), 8.06(d, 2 H, J=7 Hz), 7.55–7.23(m, 6 H), 4,78(s, 2 H), 4.55(s, 2 H), 1.53(s, 6 H).
IR($v$cm$^{-1}$, CHCl$_3$) 3530, 3330.

EXAMPLE 8

4-(α-Hydroperoxyisopropyl)benzyl 3,4,5-trimethoxyphenyl ether

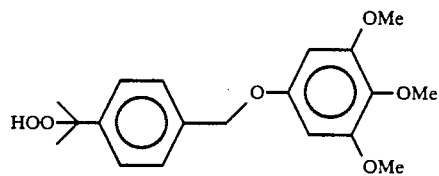

To a solution of 1.46 g (36.5 mmol) of sodium hydride contained at 60% in mineral oil in dry dimethylformamide (50 ml) was added 2.02 g (11.0 mmol) of 3,4,5-trimethoxyphenol in an atmosphere of argon, and the mixture was allowed to react at 0° C. for 15 min. To the reaction mixture was added 3.60 g (14.4 mmol) of 4-bromobenzyl bromide. The resulting mixture was reacted at room temperature for 24 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (1:1) yielded 3.28 g (9.28 mmol) of 4-bromobenzyl 3,4,5-trimethoxyphenyl ether.

To a solution of 3.28 g (9.28 mmol) of the above-obtained compound in dry tetrahydrofuran (120 ml) at −78° C. was added 1.60M hexane solution of n-butyllithium (8.70 ml, 13.9 mmol) in the atmosphere of argon, and the mixture was allowed to react for 30 min. To the solution was added 3.40 ml (46.3 mmol) of acetone, and the mixture was reacted at −78° C. for 10 min. To the reaction mixture was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with ethyl acetate-hexane (1:3) yielded 1.72 g (5.17 mmol) of 4-(α-hydroxyisopropyl)benzyl 3,4,5-trimethoxyphenylether.

To 1.72 g (5.17 mmol) of the above-obtained hydroxy compound were added 10 ml of ether, 20 ml of a 30% aqueous solution of hydrogen peroxide and 0.500 ml of concentrated sulfuric acid. The mixture was allowed to react at room temperature for 15 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 1.48 g (4.25 mmol) of 4-(α-hydroxyisopropyl)benzyl 3,4,5-trimethoxyphenyl ether.

NMR (ppm, CDCl$_3$)
8.67(bs, 1 H), 7.53–7.27(m, 4 H), 4.95(s, 2 H), 3.77(s, 9 H), 1.57(s, 3 H).
IR($\nu$cm$^{-1}$,CHCl$_3$) 3530, 3330.

EXAMPLE 9

Polyethylene glycol 4-(α-hydroperoxyisopropyl)benzyl 4-(1,3-dimethylbutyl)phenyl ether

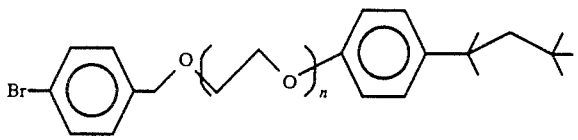

(average value for n 10)

To a solution of 2.14 g (53.4 mmol) of sodium hydride contained at 60% in mineral oil in dry dimethylformamide (120 ml) was added 5.66 g (8.76 mmol on average) of Triton X-100 in an atmosphere of argon, and the mixture was allowed to react at 40°–50° C. for 30 min. To the reaction mixture was added 4.41 g (17.6 mmol) of 4-bromobenzyl bromide, and the mixture was reacted at 60° C. for 30 min. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (4:1) yielded 2.54 g (3.12 mmol on average) of a compound of the structure shown below.

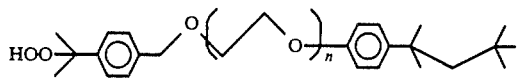

(average value for n 10)

To a solution of 2.54 g (312 mmol on average) of the above-obtained compound in dry tetrahydrofuran (80 ml) at −78° C. was added 1.60M hexane solution of n-butyllithium (4.00 ml, 6.40 mmol) in the atmosphere of argon, and the mixture was allowed to react for 30 min. To the solution was added 5.00 ml (68.1 mmol) of acetone, and the mixture was allowed to react at −78° C. for 10 min. To the reaction mixture was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-methanol (25:1) yielded 2.89 g (3.64 mmol on average) of a compound of the structure shown below.

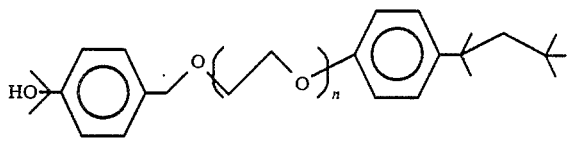

(average value for n 10)

To 2.89 g (3.64 mmol on average) of said hydroxy compound were added 10 ml of ether, 20 ml of a 30% aqueous solution of hydrogen peroxide and 0.500 ml of concentrated sulfuric acid, and the mixture was allowed to react at room temperature for 48 hours followed by addition of water and extraction with ethyl acetate. The organic layer was washed with water and then concentrated under reduced pressure. The residue thus obtained was subjected to silica gel column chromatography for separation and purification. Elution with dichloromethane-methanol (25:1) yielded 1.40 g (1.73 mmol on average) of the desired product.

NMR (ppm, CDCl$_3$)
9.07(bs, 1 H), 7.62–6.83(m, 8 H), 4.60(s, 4 H), 3.73(s, 40 H), 1.82(s, 2 H), 1.67(s, 6 H), 1.46(s, 6 H), 0.83(s, 9 H).
IR($\nu$cm$^{-1}$,CHCl$_3$) 3520.

EXAMPLE 10

3,4-Bis(2,5,8,11,14-pentaoxapentadecanyl)cumene hydroperoxide

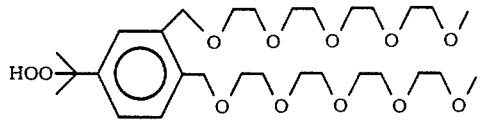

To a solution of 4.13 g (22.3 mmol) of 3,4-dimethyl-1-bromobenzene in carbon tetrachloride (160 ml) were added 8.73 g (49.0 mmol) of N-bromosuccinimide and 150 mg (0.62 mmol) of benzoyl peroxide in an atmosphere of argon, and the mixture was refluxed for 18 hours. To the reaction mixture was added water followed by extraction with benzene. The organic layer was washed with water and concentrated under reduced pressure. The residue thus obtained was subjected to silica gel column chromatography for separation and purification. Elution with hexane-dichloromethane (10:1) yielded 2.57 g (7.49 mmol) of 3,4-bis(bromomethyl)-1-bromobenzene.

Next, 3.74 g (18.0 mmol) of 3,6,9,12-tetraoxa-1-tridecanol was added to a solution of 1.92 g (48.0 mmol) of sodium hydride contained at 60% in mineral oil in dry dimethylformamide (65 ml) in the atmosphere of argon, and the mixture was allowed to react at 40°–50° C. for 30 min. Then, to the reaction mixture was added 2.57 g (7.49 mmol) of 3,4-bis(bromomethyl)-1-bromobenzene, and the mixture was reacted at room temperature for 19 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane yielded 3.08 g (5.16 mmol) of 3,4-bis(2,5,8,11,14-pentaoxapentadecanyl)-1-bromobenzene.

To a solution of 3.08 g (5.16 mmol) of the above-obtained compound in dry tetrahydrofuran (150 ml) at −78° C. was added 1.60M hexane solution of n-butyllithium (4.80 ml, 7.68 mmol) in the atmosphere of argon, and the mixture was allowed to react for 30 min. To the solution was added 1.90 ml (25.9 mmol) of acetone, and the mixture was reacted at −78° C. for 10 min. To the reaction mixture was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-methanol (50:1) yielded 2.56 g (4.44 mmol) of 3,4-bis(2,5,8,11,14-pentaoxapentadecanyl)-1-(α-hydroxyisopropyl)benzene.

To 2.56 g (4.44 mmol) of the above-obtained hydroxy compound were added 10 ml of ether, 20 ml of a 30% aqueous solution of hydrogen peroxide and 0.50 ml of concentrated sulfuric acid, and the mixture was allowed to react at room temperature for 15 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (2:1) yielded 2.26 g (3.82 mmol) of 3,4-bis(2,5,8,11,14-pentaoxapentadecanyl)cumene hydroperoxide.

NMR (ppm, CDCl$_3$)
8 12(s, 1 H), 7.53–7.21(m, 3 H), 4.56(s, 4 H),
3.68(s, 32 H), 3.35(s, 6 H), 1.51(s, 6 H).
IR($\nu$cm$^{-1}$,CHCl$_3$) 3530, 3320.

EXAMPLE 11

3,4,5-Tris(2-oxa-3-phenylpropyl)cumene hydroperoxide

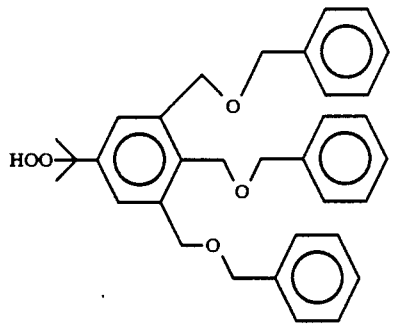

To a solution of 3.63 g (18.2 mmol) of 3,4,5-trimethyl-1-bromobenzene in carbon tetrachloride (200 ml) were added 10.7 g (60.1 mmol) of N-bromosuccinimide and 165 mg (0.68 mmol) of benzoyl peroxide in an atmosphere of argon, and the mixture was refluxed for 24 hours. To the reaction mixture was added water followed by extraction with benzene. The organic layer was washed with water and concentrated under reduced pressure. The residue thus obtained was subjected to silica gel column chromatography for separation and purification. Elution with hexane-dichloromethane (10:1) yielded 1.51 g (3.46 mmol) of 3,4,5-tris(-bromomethyl)-1bromobenzene.

To a solution of 726 mg (18.2 mmol) of sodium hydride contained at 60% in mineral oil in dry dimethylformamide (30 ml) was added 1.31 g (12.1 mmol) of benzyl alcohol in the atmosphere of argon, and the mixture was allowed to react at 40 -50° C. for 30 min. To the reaction mixture was added 1.51 g (3.46 mmol) of 3,4,5-tris(bromomethyl)-1-bromobenzene, and the mixture was reacted at room temperature for 40 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane (1:1) yielded 1.04 g (2.01 mmol) of 3,4,5-tris (2-oxa-3-phenylpropyl)-1-bromobenzene.

To a solution of 1.04 g (2.01 mmol) of the above-obtained compound in dry tetrahydrofuran (20 ml) at −78° C. was added 1.60M hexane solution of n-butyllithium (1.90 ml, 3.04 mmol) in the atmosphere of argon, and the mixture was allowed to react for 30 min. To the solution was added 1.50 ml (20.4 mmol) of acetone, and the mixture was reacted at −78° C. for 10 min. To the reaction mixture was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-methanol (100:1) yielded 917 mg (1.85 mmol) of 3,4,5-tris(2-oxa-3-phenylpropyl)-1-(α-hydroxyisopropyl)benzene.

To 917 mg (1.85 mmol) of the above-obtained hydroxy compound were added 5 ml of ether, 10 ml of a 30% aqueous solution of hydrogen peroxide and 0.25 ml of concentrated sulfuric acid, and the mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:2) yielded 831 mg (1.62 mmol) of 3,4,5-tris(2-oxa-3-phenyl-propyl)cumene hydroperoxide.

NMR (ppm, CDCl$_3$)
8.30(s, 1 H), 7.38(s, 2 H), 7.30(s, 15 H),
4.55(s, 12 H), 1.53(s, 6 H)
IR($\nu$cm$^{-1}$,CHCl$_3$) 3530, 3330.

EXAMPLE 12

1-Chloro-4-(α-hydroperoxyisopropyl)-2-(2-methoxyethoxymethoxymethyl)benzene

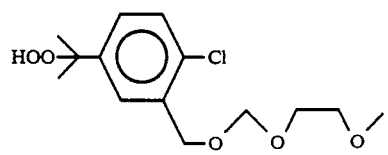

To a solution of 100 g (4.52 mmol) of 5-bromo-2-chlorobenzyl alcohol in dry dichloromethane (20 ml) were added 675 mg (5.42 mmol) of 2-methoxyethoxymethyl chloride and 1.20 ml (6.89 mmol) of N,N-diisopropylethylamine in an atmosphere of argon, and the mixture was allowed to react at room temperature for 18 hours. To the reaction solution at 0° C. was a added saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (1:5) yielded 1.23 g (3.98 mmol) of 4-bromo-1-chloro-2-(2-methoxyethoxymethoxymethyl)benzene.

To a solution of 1.23 g (3.98 mmol) of the above-obtained compound in dry tetrahydrofuran (30 ml) at −78° C. was added 1.60M hexane solution of n-butyllithium (2.99 ml, 4.78 mmol) in the atmosphere of argon, and the mixture was allowed to react for 30 min. To the solution was added 5.0 ml (68.0 mmol) of acetone, and the mixture was reacted at −78° C. for 10 min. followed by addition of saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (50:1) yielded 829 mg (2.87 mmol) of 1-chloro-4-($\alpha$-hydroxyisopropyl)-2-(2-methoxyethoxymethoxymethyl)benzene.

To 829 mg (2.87 mmol) of the above-obtained hydroxy compound were added 5.0 ml of ether, 30 ml of a 50% aqueous solution of hydrogen peroxide and 0.2 ml of concentrated sulfuric acid, and the mixture was allowed to react at room temperature for 17 hours. To the reaction mixture was added water followed by extraction with ethyl acetate. The organic layer was washed with water and then concentrated under reduced pressure. The residue thus obtained was subjected to silica gel column chromatography for separation and purification. Elution with ethyl acetate-hexane (3:1) yielded 699 mg (2.18 mmol) of 1-chloro-4-($\alpha$-hydroperoxyisopropyl)-2-(2-methoxyethoxymethoxymethyl)benzene.

NMR (ppm, CDCl$_3$)
8.21(s, 1 H), 7.41–7.08(s, 3 H), 4.73(s, 2 H),
4 52(s, 2 H), 3.82–3.43(m, 4 H), 3.35(s, 3 H),
1.56(s, 6 H).
IR($\nu$cm$^{-1}$,CHCl$_3$) 3530, 3330.

EXAMPLE 13

[4-($\alpha$-Hydroperoxyisopropyl)-2-methyl]benzyl benzyl ether

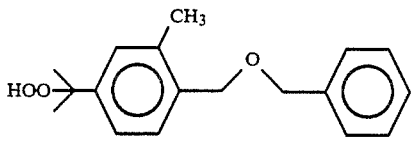

To a solution of 298 mg (7.46 mmol) of sodium hydride contained at 60% in mineral oil in dry dimethylformamide (20 ml) was added 1.00 g (4.97 mmol) of 4-bromo-2-methylbenzyl alcohol in an atmosphere of argon, and the mixture was allowed to react at 40 -50° C. for 30 min. To the reaction mixture was added 1.02 g (5.96 mmol) of benzyl bromide, and the mixture was reacted at room temperature for 17 hours. To the reaction solution at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with ethyl acetate-hexane (1:3) yielded 1.26 g (4.32 mmol) of (4-bromo-2-methyl)benzyl benzyl ether.

To a solution of 1.26 g (4.32 mmol) of the above-obtained compound in dry tetrahydrofuran (20 ml) at −78° C. was added 1.60M hexane solution of n-butyllithium (3.24 ml, 5.18 mmol) in the atmosphere of argon, and the mixture was allowed to react for 30 min. To the solution was added 5.0 ml (68.0 mmol) of acetone and the mixture was allowed to react at −78° C. for 10 min. To the solution was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-methanol (100:1) yielded 898 mg (3.32 mmol) of [4-($\alpha$-hydroxyisopropyl)-2-methyl]benzyl benzyl ether.

To 898 mg (3.32 mmol) of the above-obtained hydroxy compound were added 5.0 ml of ether, 30 ml of a 50% aqueous solution of hydrogen peroxide and 0.2 ml of concentrated sulfuric acid, and the mixture was allowed to react at room temperature for 17 hours. To the reaction mixture was added water followed by extraction with ethyl acetate. The organic layer was washed with water and then concentrated under reduced pressure. The residue thus obtained was subjected to silica gel column chromatography for separation and purification. Elution of ethyl acetate-hexane (1:4) yielded 783 mg (2.59 mmol) of [4-($\alpha$-hydroperoxyisopropyl)-2-methyl]benzyl benzyl ether.

NMR (ppm, CDCl$_3$)
8.22(br, 1 H), 7.51–7.18(m, 8 H), 4.48(s, 4 H),
2.26(s, 3 H), 1.57(s, 6 H).
IR($\nu$cm$^{-1}$,CHCl$_3$) 3530, 3320.

EXAMPLE 14

4-($\alpha$-Hydroperoxyisopropyl)-2,6-dichlorobenzyl benzyl ether

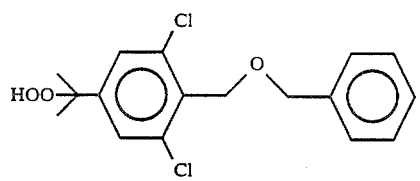

To a solution of 336 mg (8.39 mmol) of sodium hydride contained at 60% in mineral oil in dry dimethylformamide (30 ml) was added 1.43 g (5.59 mmol) of 4-bromo-2,6-dichloro-benzyl alcohol in an atmosphere of argon, and the mixture was allowed to react at 40°-50° C. for 30 min. To the reaction mixture was added 1.15 g (6.71 mmol) of benzyl bromide, and the mixture was allowed to react at room temperature for 18 hours. To the reaction solution at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (1:1) yielded 1.68 g (4.86 mmol) of (4-bromo-2,6-dichloro)benzyl benzyl ether.

To a solution of 1.68 g (4.86 mmol) of the above-obtained compound in dry tetrahydrofuran (40 ml) at −78° C. was added 1.60M hexane solution of n-butyllithium (3.65 ml, 5.83 mmol) in the atmosphere of argon, and the mixture was allowed to react for 30 min. To the solution was added 5.00 ml (68.1 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue obtained was then subjected to silica gel column chromatography for separation and purification. Elution with dichloromethane-methanol (100:1) yielded 1.17 g (3.59 mmol) of [2.6-dichloro-4-(a-hydroxyisopropyl)benzyl]-benzyl ether.

To 1.17 g (3.59 mmol) of the above-obtained hydroxy compound were added 5 ml of ether, 20 ml of a 30% aqueous solution of hydrogen peroxide and 0.50 ml of concentrated sulfuric acid. The mixture was allowed to react at room temperature for 18 hours followed by addition of water and extraction with ethyl acetate. The organic layer was washed with water. The residue obtained was then subjected to silica gel column chromatography for separation and purification. Elution with dichloromethane-methanol (100:1) yielded 870 mg (2.55 mmol) of 4-(α-hydroperoxyisopropyl)-2,6-dichlorobenzyl benzyl ether.

NMR (ppm, CDCl₃)
7.95 (s, 1 H), 7.3–7.06 (m, 7 H), 4.53 (s, 4 H), 1.57 (s, 6 H).
IR(νcm⁻¹,CHCl₃) 3530, 3330.

EXAMPLE 15

1-[4-   -Hydroperoxyisopropyl)benzenesulfonyl]butane

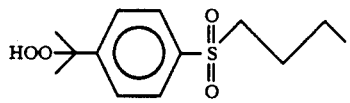

To a solution of 2.92 g (15.9 mmol) of 1-iodated butane in dry dichloromethane (30 ml) were added 5.34 g (52.9 mmol) of triethylamine and 1.50 g (13.2 mmol) of 4-bromothiophenol in an atmosphere of argon, and the mixture was allowed to react at room temperature for 18 hours. To the solution was added water followed by extraction with ethyl acetate. The organic layer was washed with water and then concentrated under reduced pressure. The residue thus obtained was subjected to silica gel column chromatography for separation and purification. Elution with dichloromethane-hexane (1:4) yielded 3.28 g (12.8 mmol) of 4-bromophenyl butyl sulfide.

To a solution of 3.28 g (12.8 mmol) of the above-obtained compound in dry tetrahydrofuran (30 ml) at −78° C. was added 1.60M hexane solution of n-butyllithium (9.63 ml, 15.4 mmol) in the atmosphere of argon, and the mixture was allowed to react for 30 min. To the solution was added 4.0 ml (54.5 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 2.32 g (9.85 mmol) of 4-(α-hydroxyisopropyl)phenyl butyl sulfide.

To 2.32 g (9.85 mmol) of the above-obtained hydroxy compound were added 20 ml of ether, 20 ml of a 30% aqueous solution of hydrogen peroxide and 0.50 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (3:1) yielded 1.83 g (7.27 mmol) of 1-[4-(α-hydroperoxyisopropyl)benzenesulfonyl]butane.

NMR (ppm, CDCl₃)
7.83(s, 1 H), 7.72–7.13(m, 4 H), 4.03–3.75 (m, 2 H), 1.60(s, 6 H), 1.37–0.82(m, 7 H).
IR(νcm⁻¹,CHCl₃) 3400.

EXAMPLE 16

N,N-Dimethyl[4-(α-hydroperoxyisopropyl)benzene]sulfoamide

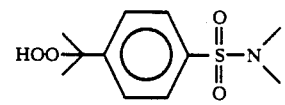

To a solution of 2.92 g (35.8 mmol) of dimethylamine hydrochloride in 50 ml of dry pyridine was added 5.20 g (20.4 mmol) of 4-bromobenzenesulfonyl chloride in an atmosphere of argon, and the mixture was allowed to react at 0° C. for 2 hours. To the solution was added water followed by extraction with ethyl acetate. The organic layer was washed with water and then concentrated under reduced pressure. The residue thus obtained was subjected to silica gel column chromatography for separation and purification. Elution with dichloromethane yielded 5.01 g (19.0 mmol) of N,N-dimethyl-(4-bromobenzene)sulfoamide.

To a solution of 5.01 g (19.0 mmol) of the above-obtained compound in 50 ml of dry tetrahydrofuran at −78° C. was added 1.60M hexane solution of n-butyllithium (15.0 ml, 24.0 mmol) in the atmosphere of argon, and the mixture was allowed to react for 30 min. To the solution was added 6.0 ml (81.7 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with ethyl acetatehexane (1:2) yielded 3.42 g (14.1 mmol) of N,N-dimethyl-[4-(α-hydroxyisopropyl)benzene]sulfoamide.

To 3.42 g (14.1 mmol) of the above-obtained hydroxy compound were added 20 ml of ether, 20 ml of a 30% aqueous solution of hydrogen peroxide and 0.500 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with dichloromethane-methanol (50:1) yielded 2.71 g (10.5 mmol) of N,N-dimethyl-[4-(α-hydroperoxyisopropyl)-benzene]sulfoamide.

NMR (ppm, CDCl₃)
7.83–7.10(m, 4 H), 7.67(s, 1 H), 2.75(s, 6 H), 1.66(s, 6 H).
IR($\nu$cm$^{-1}$,CHCl₃) 3400.

EXAMPLE 17

[4-(α-Hydroperoxyisopropyl)benzene]sulfonyl-3,5,8-trioxanonane

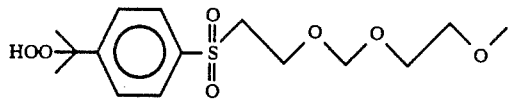

To a solution of 1.20 g (6.35 mmol) of 4-bromothiophenol in dry tetrahydrofuran (30 ml) was added 1.62 g (7.62 mmol) of 1-bromo-3,5,8-trioxanonane in an atmosphere of argon, and the mixture was allowed to react at room temperature for 24 hours. To the solution was added water followed by extraction with ethyl acetate. The organic layer was washed with water and then concentrated under reduced pressure. The residue thus obtained was subjected to silica gel column chromatography for separation and purification. Elution with dichloromethane yielded 1.92 g (5.97 mmol) of 4-bromophenyl-2-(2-methoxyethoxymethoxy)ethyl sulfide.

To a solution of 1.92 g (5.97 mmol) of the above-obtained compound in dry tetrahydrofuran (30 ml) at −78° C. was added 1.60M hexane solution of n-butyllithium (4.5 ml, 7.16 mmol) in the atmosphere of argon, and the mixture was allowed to react for 30 min. To the solution was added 4.0 ml (54.5 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (50:1) yielded 1.33 g (4.42 mmol) of 4-(α-hydroxyisopropyl)phenyl 2-(2-methoxyethoxymethoxy)ethyl sulfide.

To 1.33 g (4.42 mmol) of the above-obtained hydroxy compound were added 10 ml of ether, 20 ml of a 30% aqueous solution of hydrogen peroxide and 0.50 ml of concentrated sulfuric acid, and the mixture was allowed to react at room temperature for 18 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (3:1) yielded 1.16 g (3.32 mmol) of 1-[4-(α-hydroperoxyisopropyl)benzene]sulfonyl-3,5,8-trioxanonane.

NMR (ppm, CDCl₃)
7.93 (s, 1 H), 7.43–7.01 (m, 4 H), 4.68 (s, 2 H), 4.88–3.77 (m, 8 H), 3.34 (s, 3 H), 1.62 (s, 6 H).
IR($\nu$cm$^{-1}$,CHCl₃) 3520, 3330.

EXAMPLE 18

N-[4-(α-Hydroperoxyisopropyl)benzenesulfonyl]morpholine

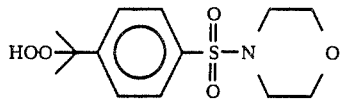

To a solution of 1.67 g (19.14 mmol) of morpholine in 50 ml of dry pyridine was added 3.26 g (12.76 mmol) of 4-bromobenzenesulfonyl chloride in an atmosphere of argon, and the mixture was allowed to react at 0° C for 3 hours. To the solution was added water followed by extraction with ethyl acetate. The organic layer was washed with water and then concentrated under reduced pressure. The residue thus obtained was subjected to silica gel column chromatography for separation and purification. Elution with dichloromethane yielded 3.45 g (11.3 mmol) of N-(4-bromobenzenesulfonyl)morpholine.

To a solution of 3.45 g (11.3 mmol) of the above-obtained compound in 50 ml of dry tetrahydrofuran at −78° C. was added 1.60M hexane solution of n-butyllithium (8.5 ml, 13.6 mmol) in the atmosphere of argon, and the mixture was allowed to react for 30 min. To the solution was added 4.0 ml (54.5 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with ethyl acetate-hexane (1:2) yielded 2.49 g (8.37 mmol) of N-[4-(α-hydroxyisopropyl)benzenesulfonyl]morpholine.

To 2.49 g (8.37 mmol) of the above-obtained hydroxy compound were added 20 ml of ether, 20 ml of a 30% aqueous solution of hydrogen peroxide and 0.500 ml of concentrated sulfuric acid. The mixture was allowed to react at room temperature for 17 hours followed by addition of water and extraction with ethyl acetate. The organic layer was washed with water and then concentrated under reduced pressure. The residue thus obtained was subjected to silica gel column chromatography for separation and purification. Elution with dichloromethane-methanol (50:1) yielded 1.99 g (6.35 mmol) of N-[4-(α-hydroperoxyisopropyl)benzenesulfonyl]morpholine.

NMR (ppm, CDCl₃)
7.80 (s, 1 H), 7.79–7.08 (m, 4 H), 3.83–3.60 (m, 4 H) 3.10–2.87 (m, 4 H), 1.58 (s, 6 H).
IR($\nu$cm$^{-1}$,KBr) 3400.

EXAMPLE 19

1,3-Bis[4-(α-hydroperoxyisopropyl)phenyl]propane

To a solution of 3.40 g (17.1 mmol) of 4'-bromoacetophenone in ethanol (140 ml) was added 3.80 g (20.5 mmol) of 4-bromobenzaldehyde followed by further addition at 0° C. of an aqueous solution of 4.19 g (105 mmol) of sodium hydroxide (14 ml). The mixture was allowed to react at room temperature for one hour, then precipitates formed were collected by filtration and washed with cooled dichloromethane. There was obtained 5.30 g (14.5 mmol) of the crystals.

To a solution of 5.30 g (14.5 mmol) of the above-obtained compound in toluene (50 ml) was added 1.20 g of palladium-on-carbon, and the mixture was vigorously stirred in an atmosphere of hydrogen. The reaction was carried out at room temperature for 6 hours, then insoluble matter was removed by filtration, and the solution thus obtained was concentrated under reduced pressure.

To 4.68 g of the compound thus obtained was added methanol (100 ml) followed by addition at 0° C. of 1.53 g (40.4 mmol) of sodium borohydride. The mixture was allowed to react at room temperature for 3 hours. To the solution was added water followed by extraction with ethyl acetate. The organic layer was washed with water and then concentrated under reduced pressure. To 4.51 g of the compound thus obtained was again added toluene (50 ml) followed by addition of 1.05 g of palladium-on-carbon. The mixture was vigorously stirred in the atmosphere of hydrogen. The reaction was carried out at room temperature for 10 hours, insoluble matter was removed by filtration, and the solution thus obtained was concentrated under reduced pressure. The residue thus obtained was subjected to silica gel column chromatography for separation and purification. There was produced 692 mg (1.95 mmol) of 1,3-bis(4-bromophenyl)propane.

Next, to a solution of 692 mg (1.95 mmol) of the above-obtained compound in dry tetrahydrofuran (14 ml) at −78° C. was added a 1.60M hexane solution of a n-butyllithium (3.00 ml, 4.80 mmol), and the mixture was allowed to react for 30 min. To the solution was added 1.50 ml (20.4 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (25:1) yielded 505 mg (1.62 mmol) of 1,3-bis[4-(α-hydroxyisopropyl)phenyl]propane.

To 505 mg (1.62 mmol) of the above-obtained compound were added 5 ml of ether, 10 ml of a 30% aqueous solution of hydrogen peroxide and 0.25 ml of concentrated sulfuric acid. The mixture was allowed to react at room temperature for 18 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 510 mg (1.48 mmol) of 1,3-bis[4-(α-hydroperoxyisopropyl)phenyl]propane.

NMR (ppm, CDCl₃)
8.05(s, 2 H), 7.36-7.02 (m, 8 H), 2.63-2.31(m, 4 H), 2.14-1.86(m, 2 H), 1.53(s, 12 H).
IR(νcm⁻¹,CHCl₃) 3530, 3330.

EXAMPLE 20

2,2-Bis[4-(α-hydroperoxyisopropyl)phenyl]-3,5,8-trioxanonane

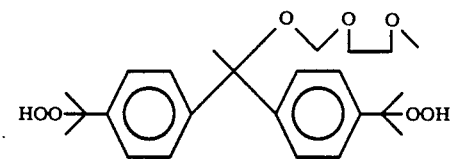

To a solution of 6.43 g (18.1 mmol) of 1,1-bis(4-bromophenyl)ethanol in dry dichloromethane (50 ml) were added 2.50 ml (21.9 mmol) of β-methoxyethoxymethyl chloride and 4.8 ml (27.6 mmol) of N,N-diisopropylethylamine in an atmosphere of argon, and the mixture was refluxed for 15 hours.

To the solution was added water followed by extraction with dichloromethane. The organic layer was washed with water and concentrated under reduced pressure. The residue thus obtained was subjected to silica gel column chromatography for separation and purification. Elution with dichloromethane yielded 6.55 g (14.8 mmol) of 2,2-bis-(4-bromophenyl)-3,5,8-trioxanonane.

To a solution of 6.55 g (14.8 mmol) of the above-obtained compound in dry tetrahydrofuran (200 ml) at −78° C. was added a 1.60M hexane solution of n-butyllithium (23.0 ml, 36.8 mmol) in the atmosphere of argon, and the mixture was allowed to react for 30 min. To the solution was added 11.0 ml (150 mmol) of acetone, and the mixture was allowed to react at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (50:1) yielded 4.67 g (11.6 mmol) of 2,2-bis-[4-(α-hydroxyisopropyl)phenyl-3,5,8-trioxanonane.

To 4.67 g (11.6 mmol) of the above-obtained hydroxy compound were added 20 ml of ether, 40 ml of 30% aqueous solution of hydrogen peroxide and 1.00 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 4.08 g (9.40 mmol) of 2,2-[bis4-(α-hydroperoxyisopropyl)phenyl]-3,5,8-trioxanonane.

NMR (ppm, CDCl₃)
8.05(s, 2 H), 7.51-7.22(m, 8 H), 4.68(s, 2 H),
3.33(m, 4 H), 3.32(s, 3 H), 1.92(s, 3 H),
1.51(s, 12 H)
IR(νcm⁻¹,CHCl₃) 3530, 3320

EXAMPLE 21

1,7-Bis[4-(α-hydroperoxyisopropyl)phenyl]-4-hydroxyheptane

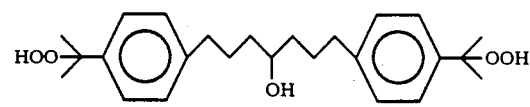

To a solution of 3.06 g (80.5 mmol) of lithium aluminum hydride in dry diethyl ether (150 ml) at 0° C. was added 4.13 g (17.9 mmol) of diethyl 4-oxopimerate in an atmosphere of argon, and the mixture was allowed to react at room temperature for 18 hours. To the reaction mixture cooled to 0° C. was added saturated aqueous solution of ammonium chloride, and precipitates formed were removed by filtration. The solution thus obtained was concentrated under reduced pressure, and the residue was subjected to silica gel column chromatography for separation and purification.

Elution with dichloromethane-methanol (5:1) yielded 1.62 g (10.9 mmol) of 1,4,7-heptatriol.

To a solution of 1.62 g (10.9 mmol) of the above-obtained compound in dry pyridine (100 ml) was added 4.57 g (24.0 mmol) of p-toluenesulfonyl chloride at room temperature in the atmosphere of argon, and the mixture was allowed to react for 20 hours.

To the solution was added water followed by extraction with dichloromethane. The organic layer was washed with water and concentrated under reduced pressure. The residue thus obtained was subjected to silica gel column chromatography for separation and purification. Elution with dichloromethane-methanol (100:1) yielded 3.58 g (7.85 mmol) of 1,7-bis(p-toluenesulfoxy)-4-heptanol.

To a solution of 3.58 g (7.85 mmol) of the above-obtained compound in dry dimethylformamide (100 ml) were added 2.39 g (8.70 mmol) of tert-butyldiphenylsilyl chloride and 1.42 g (20.8 mmol) of imidazole, and the mixture was allowed to react at room temperature for 8 hours. To the solution was added water followed by extraction with benzene. The organic layer was washed with water and concentrated under reduced pressure. The residue thus obtained was subjected to silica gel column chromatography for separation and purification. From the eluate with dichloromethanehexane (1:1) was afforded 4.74 g (6.85 mmol) of 1,7-bis(p-toluenesulfoxy)-4-(tert-butyldiphenylsiloxy)heptane.

To a solution of 4.74 g (6.85 mmol) of the above-obtained compound in acetone (200 ml) was added 4.18 g (27.9 mmol) of sodium iodide, and the mixture was refluxed for 18 hours. To the solution was added water followed by extraction with benzene. The organic layer was washed with water and concentrated under reduced pressure. The residue thus obtained was subjected to silica gel column chromatography for separation and purification. From the eluate with dichloromethane-hexane (1:5) was afforded 3.44 g (5.68 mmol) of 1,7-diiodo-4-(tert-butyldiphenylsiloxy)heptane.

To a solution of 3.42 g (14.5 mmol) of 1,4-dibromobenzene in dry tetrahydrofuran (100 ml) at −78° C. was added a 1.60M hexane solution of n-butyllithium (9.10 ml, 14.6 mmol) in the atmosphere of argon, and the mixture was allowed to react for 30 min. To the solution was added a solution of 3.44 g (5.68 mmol) of 1,7-diiodo-4-(tert-butyldiphenylsiloxy)heptane previously produced in dry tetrahydrofuran (35 ml). The temperature was raised from −78° C. to room temperature over 9 hours, and the reaction was allowed to proceed at room temperature for 15 hours. To the reaction mixture was added a saturated aqueous solution of ammonium chloride followed by extraction with benzene. The organic layer was washed with water and concentrated under reduced pressure. The residue thus obtained was subjected to silica gel column chromatography for separation and purification. From the eluate with dichloromethane-hexane (1:5) was afforded 1.05 g (1.58 mmol) of 1,7-bis(4-bromophenyl)-4-(tert-butyldiphenylsiloxy)-heptane.

Further, to a solution of 1.05 g (1.58 mmol) of 1,7-bis(4-bromophenyl)-4-(tert-butyldiphenylsiloxy)heptane in dry tetrahydrofuran (50 ml) was added a 1.60M hexane solution of n-butyllithium (2.15 ml, 3.44 mmol) in the atmosphere of argon, and the mixture was allowed to react at −78° C. for 30 min. To the solution was added 1.20 ml (16.3 mmol) of acetone, and the mixture was reacted at −78° C. for 10 min. followed by addition of a saturated aqueous solution of ammonium chloride and extraction with ethyl acetate. The organic layer was washed with water and concentrated under reduced pressure. The residue thus obtained was subjected to silica gel column chromatography for separation and purification. Elution with dichloromethane-methanol (100:1) yielded 728 mg (1.23 mmol) of 1,7-bis[4-(α-hydroxyisopropyl)phenyl]-4-(tert-butyldiphenylsiloxy)heptane.

Next, to 728 mg (1.23 mmol) of the above-obtained compound were added 5 ml of ether, 10 ml of a 30% aqueous solution of hydrogen peroxide and 0.25 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:2) yielded 658 mg (1.06 mmol) of 1,7-bis[4-(α-hydroperoxyisopropyl)phenyl]-4-(tert-butyldiphenylsiloxy)heptane.

Further, to a solution of 658 mg (1.06 mmol) of the above-obtained compound in dry tetrahydrofuran (20 ml) was added a 1.0M tetrahydrofuran solution of tetrabutylammonium fluoride (2.50 ml, 2.5 mmol), and the mixture was allowed to react at room temperature for 6 hours. To the solution was added water followed by extraction with ethyl acetate. The organic layer was washed with water and concentrated under reduced pressure. The residue thus obtained was subjected to silica gel column chromatography for separation and purification. Elution with dichloromethane-methanol (50:1) yielded 406 mg (0.976 mmol) of 1,7-bis[4-(α-hydroperoxyisopropyl)phenyl]-4-hydroxyheptane.

NMR (ppm, CDCl$_3$)
8.11(s, 2 H) 7.39–7.05(m 8 H) 3.66–3.28(m, 1 H), 2.59–2.24(m, 4 H), 2.11–1.82(m, 8 H).
IR ($v$cm$^{-1}$, CHCl$_3$) 3600, 3530, 3400.

EXAMPLE 22

Bis[4-(α-hydroperoxyisopropyl)benzyl]ether

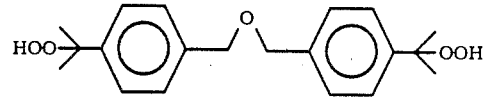

To a solution of 27.4 g (685 mmol) of sodium hydride contained at 60% in mineral oil in dry dimethylformamide (425 ml) was added 42.4 g (227 mmol) of 4-bromobenzyl alcohol in an atmosphere of argon, and the mixture was allowed to react at 40–50° C. for 30 min. Then, 62.4 g (250 mmol) of 4-bromobenzyl bromide was added, and the mixture was reacted at room temperature for 15 hours. The reaction mixture was added to ice water, and the mixture was extracted with ethyl acetate.

The organic layer was washed with water and concentrated under reduced pressure. The residue thus obtained was subjected to silica gel column chromatography for separation and purification. Elution with dichloromethane-hexane (1:1) yielded 72.7 g (204 mmol) of 4-bromobenzyl ether.

To a solution of 4.73 g (13.3 mmol) of the above-obtained compound in dry tetrahydrofuran (100 ml) at −78° C. was added a 1.60M hexane solution of n-butyllithium (21.0 ml, 33.6 mmol) in the atmosphere of argon, and the mixture was allowed to react for 30 min. To the solution was added 10.0 ml (136 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 3.30 g (10.5 mmol) of 4-(α-hydroxyisopropyl)benzyl ether.

To 3.30 g (10.5 mmol) of the above-obtained hydroxy compound were added 15 ml of ether, 30 ml of a 30% aqueous solution of hydrogen peroxide and 0.75 ml of concentrated sulfuric acid. The mixture was allowed to react at room temperature for 16 hours followed by addition of water and extraction with ethyl acetate. The organic layer was washed with water and concentrated under reduced pressure. The residue thus obtained was subjected to silica gel column chromatography for separation and purification. Elution with ethyl acetate-hexane (1:2) yielded 3.35 g (9.67 mmol) of bis[4-(α-hydroperoxyisopropyl)benzyl]ether.

NMR (ppm, CDCl$_3$)
8.00(s, 2 H), 7.45–7.13(m, 8 H), 4.47(s, 4 H) 1.53(s, 12 H).
IR ($\nu$cm$^{-1}$, CHCl$_3$) 3530, 3330.

EXAMPLE 23

1,12-Bis[4-(α-hydroperoxyisopropyl)phenyl]-2,5,8,11-tetraoxadodecane

To a solution of 355 mg (8.88 mmol) of sodium hydride contained at 60% in mineral oil in dry dimethylformamide (60 ml) was added 851 mg (5.67 mmol) of triethylene glycol in an atmosphere of argon, and the mixture was reacted at 40°–50° C. for 30 min. followed by addition of 3.37 g (13.5 mmol) of 4-bromobenzyl bromide. The mixture was allowed to react at room temperature for 18 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane yielded 2.51 g (5.14 mmol) of 1,12-bis(4-bromophenyl)-2,5,8,11-tetraoxadodecane.

To a solution of 2.51 g (5.14 mmol) of the above-obtained compound in dry tetrahydrofuran (50 ml) at −78° C. was added a 1.60M hexane solution of n-butyllithium (8.00 ml, 12.8 mmol) in the atmosphere of argon, and the mixture was allowed to react for 30 min. To the solution was added 4.00 ml (54.5 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification.

Elution with dichloromethane-methanol (25:1) yielded 1.99 g (4.42 mmol) of 1,12-bis[4-(α-hydroxyisopropyl)phenyl]-2,5,8,11-tetraoxadodecane.

To 1.99 g (4.42 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 15 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (2:1) yielded 1.84 9 (3.82 mmol) of 1,12-bis[4-(α-hydroperoxyisopropyl)phenyl]-2,5,8,11-tetraoxadodecane.

NMR (ppm, CDCl$_3$)
7.93(s, 2 H), 7.47–7.17(m, 8 H), 4.50(s, 4 H), 3.61(s, 12 H), 1.53(s, 12 H).
IR ($\nu$cm$^{-1}$, CHCl$_3$) 3530, 3330.

EXAMPLE 24

1,21-Bis[4-(α-hydroperoxyisopropyl)phenyl]-2,5,8,11,14,17,20-heptaoxaheneicosane

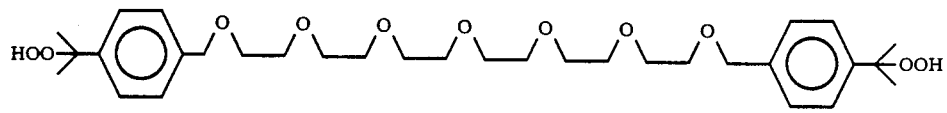

To a solution of 766 mg (19.2 mmol) of sodium hydride contained at 60% in mineral oil in dry dimethylformamide (40 ml) was added 1.80 g (6.38 mmol) of hexaethylene glycol in an atmosphere of argon, and the mixture was allowed to react at 40°–50° C. for 30 min. Then, 3.51 g (14.0 mmol) of 4-bromobenzyl bromide was added, and the mixture was allowed to react at room temperature for 16 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane yielded 3.64 g (5.87 mmol) of 1,21-bis(4-bromophenyl)-2,5,8,11,14,17,20-heptaoxaheneicosane.

To a solution of 3.64 g (5.87 mmol) of the above-obtained compound in dry tetrahydrofuran (70 ml) at −78° C. was added a 1.60M hexane solution of n-butyllithium (9.20 ml, 14.7 mmol) in the atmosphere of argon, and the mixture was allowed to react for 30 min. To the solution was added 4.40 ml (59.9 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (25:1) yielded 2.82 g (4.87 mmol) of 1,21-bis[4-(α-hydroxyisopropyl)phenyl]-2,5,8,11,14,17,20-heptaoxaheneicosane.

To 2.82 g (4.87 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 18 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (2:1) yielded 2.71 g (4.44 mmol) of 1,21-bis[4-(α-hydroperoxyisopropyl)phenyl]-2,5,8,11,14,17,20-heptaoxaheneicosane.

NMR (ppm, CDCl$_3$)
8.07(bs, 2 H), 7.50–7.17(m, 8 H), 4.52(s, 4 H), 3.63(s, 24 H), 1.57(s, 12 H).
IR (νcm$^{-1}$, CHCl$_3$) 3530, 3340.

EXAMPLE 25

Bis-[4-(α-hydroperoxyisopropyl)phenyl]polyethylene glycol

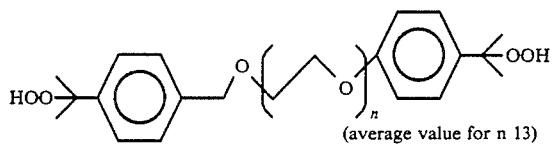
(average value for n 13)

To a solution of 633 mg (15.8 mmol) of sodium hydride contained at 60% in mineral oil in dry dimethylformamide (50 ml) was added 4.06 g (6.76 mmol on average) of polyethylene glycol with an average molecular weight of 600 in an atmosphere of argon, and the mixture was allowed to react at 40°–50° C. for 30 min. Then, 5.12 g (20.4 mmol) of 4-bromobenzyl bromide was added, and the mixture was reacted at room temperature for 19 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-methanol (50:1) yielded 2.74 g (3.00 mmol on average) of a compound having the structure shown below.

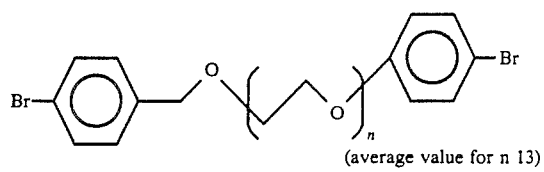
(average value for n 13)

To a solution of 2.74 g (3.00 mmol on average) of the above-obtained compound in dry tetrahydrofuran (60 ml) at −78° C. was added 1.60M hexane solution of n-butyllithium (5.70 ml, 9.12 mmol) in the atmosphere of argon, and the mixture was allowed to react for 30 min. To the solution was added 2.50 ml (34.0 mmol) of acetone, and the mixture was allowed to react at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (20:1) yielded 1.36 g (1.56 mmol on average) of a compound having the formula shown below.

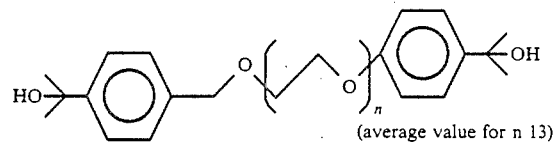
(average value for n 13)

To 1.36 g (1.56 mmol on average) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with dichloromethane-hexane (20:1) yielded 869 mg (0.961 mmol on average) of a compound having the formula shown below.

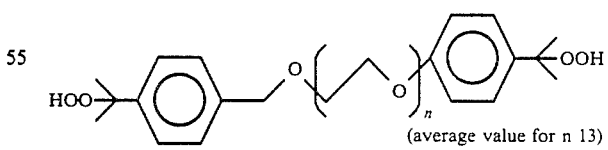
(average value for n 13)

NMR (ppm, CDCl$_3$)
8.09(s, 2 H), 7.48–7.14(m, 8 H), 4.53(s, 4 H), 3.62(s, 52 H), 1.53(s, 12 H).
IR (νcm$^{-1}$, CHCl$_3$) 3530, 3330.

EXAMPLE 26

1,14-Bis[4-(α-hydroperoxyisopropyl)phenyl]-2,13-dioxatetradecane

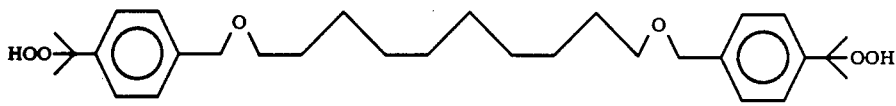

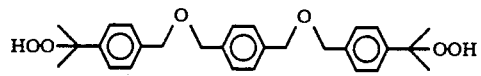

To a solution of 851 mg (21.3 mmol) of sodium hydride contained at 60% in mineral oil in dry dimethylformamide (60 ml) was added 1.21 g (6.94 mmol) of 1,10-decanediol in an atmosphere of argon, and the mixture was allowed to react at 40°-50° C. for 30 min. Then, 4.23 g (16.9 mmol) of 4-bromobenzyl bromide was added to the solution, and the mixture was reacted at room temperature for 18 hours. To the solution at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (1:1) yielded 3.09 g (6.04 mmol) of 1,14-bis(4-bromophenyl)-2,13-dioxatetradecane.

To a solution of 3.09 g (6.04 mmol) of the above-obtained compound in dry tetrahydrofuran (80 ml) at −78° C. was added a 1.60M hexane solution of n-butyllithium (9.40 ml, 15.0 mmol) in the atmosphere of argon, and the mixture was allowed to react for 30 min. To the solution was added 5.00 ml (68.1 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (50:1) yielded 1.10 g (2.34 mmol) of 1,14-bis[4-(α-hydroxyisopropyl)phenyl]-2,13-dioxatetradecane.

To 1.10 g (2.34 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 1.04 g (2.07 mmol) of 1,14-bis[4-(α-hydroperoxyisopropyl)phenyl]-2,13-dioxatetradecane.

NMR (ppm, CDCl$_3$)
7.97(bs, 2 H), 7.47–7.10(m, 8 H), 4.40(s, 4 H), 3.40(t, 4H, J=6 Hz), 1.5(s, 12 H), 1.23(bs, 16 H)
IR ($v$cm$^{-1}$, CHCl$_3$) 3530, 3230.

EXAMPLE 27

1,4-Bis[3-(4-(α-hydroperoxyisopropyl)phenyl]-2-oxapropyl]-benzene

To a solution of 951 mg (23.8 mmol) of sodium hydride contained at 60% in mineral oil in dry dimethylformamide (50 ml) was added 2.64 g (14.1mmol) of 4-bromobenzyl alcohol in an atmosphere of argon, and the mixture was allowed to react at 40°-50° C. for 30 min. Then, 1.62 g (6.14 mmol) of α,α'-dibromo-p-xylene was added, and the mixture was reacted at room temperature for 19 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane-hexane (4:1) yielded 1.83 g (3.84 mmol) of 1,4-bis[3-(4-bromophenyl)-2-oxapropyl]benzene.

To a solution of 1.83 g (3.84 mmol) of the above-compound in dry tetrahydrofuran (60 ml) at −78° C. was added a 1.60M hexane solution of n-butyllithium (6.00 ml, 9.60 mmol) in the atmosphere of argon, and the mixture was allowed to react for 30 min. To the solution was added 3.00 ml (40.9 mmol) of acetone, and the mixture was allowed to react at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 1.22 g (2.81 mmol) of 1,4-bis[3-[4-(α-hydroxyisopropyl)phenyl]-2-oxapropyl]-benzene.

To 1.22 g (2.81 mmol) of the above-obtained hydroxy compound were added 10 ml of ether, 20 ml of a 30% aqueous solution of hydrogen peroxide and 0.500 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:3) yielded 1.11 g (2.38 mmol) of 1,4-bis[3-[4-(α-hydroperoxyisopropyl)phenyl]-2-oxapropyl]benzene.

NMR (ppm, CDCl$_3$)
8.10(bs, 2 H), 7.48–7.17(m, 12 H), 4.45(s, 8 H), 1.52(s, 12 H).
IR ($v$cm$^{-1}$, CHCl$_3$) 3530, 3330.

EXAMPLE 28

1,13-Bis[4-(α-hydroperoxyisopropyl)phenyl]-7-hydroxy-4,10-dioxatridecane

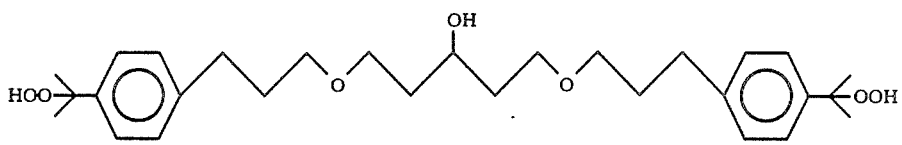

To a solution of 1.22 g (5.97 mmol) of diethyl 3-hydroxyglutarate in dry dimethylformamide (30 ml) were added 1.95 g (7.09 mmol) of tert-butyldiphenylsilyl chloride and 1.41 g (20.7 mmol) of imidazole in an atmosphere of argon, and the mixture was allowed to react at room temperature for 10 hours. To the solution was added water followed by extraction with benzene. The organic layer was washed with water and concentrated under reduced pressure. The residue thus obtained was subjected to silica gel column chromatography for separation and purification. From the eluate with dichloromethane-hexane (1:1) was afforded 2.54 g (5.75 mmol) of diethyl 3-(tert-butyldiphenylsiloxy)-glutarate.

Next, to a solution of 2.54 g (5.75 mmol) of said compound in dry diethyl ether (100 ml) at 0° C. was added 562 mg (14.8 mmol) of lithium aluminum hydride in the atmosphere of argon, and the mixture was allowed to react at room temperature for 3 hours. To the reaction mixture cooled to 0° C. was added a saturated aqueous solution of ammonium chloride, and precipitates formed were removed by filtration. The solution obtained was concentrated under reduced pressure, and the residue was subjected to silica gel column chromatography for separation and purification. Elution with dichloromethane-methanol (10:1) yielded 1.59 g (4.44 mmol) of 3-(tert-butyldiphenylsiloxy)-1,5-pentadiol. Further, to a solution of 1.59 g (4.44 mmol) of the above-obtained compound in dry pyridine (100 ml) was added 1.93 g (10.1 mmol) of p-toluenesulfonyl chloride, and the mixture was allowed to react at room temperature for 18 hours. To the solution was added water followed by extraction with dichloromethane. The organic layer was washed with water and concentrated under reduced pressure. The residue thus obtained was subjected to silica gel column chromatography for separation and purification. Elution with dichloromethane-methanol (100:1) yielded 2.56 g (3.84 mmol) of 1,5-bis(p-toluenesulfoxy)-3-(tert-butyldiphenylsiloxy)-pentane.

Then, to a solution of 635 mg (15.9 mmol) of sodium hydride contained at 60% in mineral oil in dry dimethylformamide (50 ml) was added 2.26 g (10.5 mmol) of 3-(4-bromophenyl)-1-propanol in the atmosphere of argon, and the mixture was allowed to react at 100° C. for 30 min. To the reaction mixture was added 2.56 g (3.84 mmol) of 1,5-bis(p-toluenesulfoxy)-3-(tert-butyldiphenylsiloxy)pentane, and the mixture was reacted at 100° C. for 16 hours. To the reaction mixture at 0° C. was added a saturated aqueous solution of ammonium chloride followed by extraction with benzene. The organic layer was washed with water and then concentrated under reduced pressure. The residue thus obtained was subjected to silica gel column chromatography for separation and purification. Elution with dichloromethane-hexane (1:2) yielded 1.27 g (1.69 mmol) of 1,13-bis(4-bromophenyl)-7-(tert-butyldiphenylsiloxy)-4,10-dioxatridecane.

To a solution of 1.27 g (1.69 mmol) of the above-obtained compound in dry tetrahydrofuran (50 ml) at −78° C. was added a 1.60M hexane solution of n-butyllithium (2.30 ml, 3.68 mmol) in the atmosphere of argon, and the mixture was allowed to react for 30 min. To the solution was added 1.50 ml (20.4 mmol) of acetone, and the mixture was reacted at −78° C. for 10 min. followed by addition of a saturated aqueous solution of ammonium chloride and extraction of ethyl acetate. The organic layer was washed with water and then concentrated under reduced pressure. The residue thus obtained was subjected to silica gel column chromatography for separation and purification. Elution with dichloromethane-methanol (50:1) yielded 1.05 g (1.48 mmol) of 1,13-bis[4-(α-hydroxyisopropyl)phenyl]-7-(tert-butyldiphenylsiloxy)-4,10-dioxatridecane.

To 1.05 g (1.48 mmol) of the above-obtained hydroxy compound were added 10 ml of ether, 20 ml of a 30% aqueous solution of hydrogen peroxide and 0.500 ml of concentrated sulfuric acid. The mixture was allowed to react at room temperature for 12 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 1.04 g (1.40 mmol) of 1,13-bis[4-(α-hydroperoxyisopropyl)phenyl]-7-(tert-butyldiphenylsiloxy)-4,10-dioxatridecane.

Next, to a solution of 1.04 g (1.40 mmol) of the above-obtained compound in dry tetrahydrofuran (15 ml) was added 1.0M tetrahydrofuran solution of tetrabutylammonium fluoride (2.80 ml, 2.80 mmol) in the atmosphere of argon, and the mixture was allowed to react at room temperature for 6 hours. To the solution was added water followed by extraction with ethyl acetate. The organic layer was washed with water and then concentrated under reduced pressure. The residue thus obtained was subjected to silica gel column chromatography for separation and purification. Elution with dichloromethane-methanol (25:1) yielded 621 mg (1.23 mmol) of 1,13-bis[4-(α-hydroperoxyisopropyl)phenyl]-7-hydroxy-4,10-dioxatridecane.

NMR (ppm, CDCl₃)
8.03(s, 2 H), 7.38–7.04(m, 8 H), 3.62–3.31(m, 9 H), 2.59–2.30(m, 4 H), 2.06–1.84(m, 8 H), 1.52(s, 12 H).
IR($\nu$cm$^{-1}$, CHCl₃) 3600, 3530, 3400.

EXAMPLE 29

1,6-Bis[4-(α-hydroperoxyisopropyl)phenyl]-2,5-dioxahexane

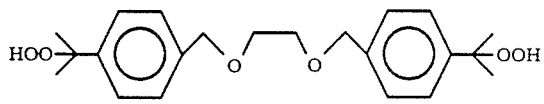

To a solution of 603 mg (15.1 mmol) of sodium hydride contained at 60% in mineral oil in dry dimethylformamide (50 ml) was added 259 mg (4.17 mmol) of ethylene glycol in an atmosphere of argon, and the mixture was allowed to react at 40°–50° C. for 30 min.

Then, 2.69 g (10.8 mmol) of 4-bromobenzyl bromide was added, and the mixture was reacted at room temperature for 20 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with dichloromethane yielded 1.57 g (3.93 mmol) of 1,6-bis(4-bromophenyl)-2,5-dioxahexane.

To a solution of 1.57 g (3.93 mmol) of the above-obtained compound in dry tetrahydrofuran (40 ml) at −78° C. was added 1.60M hexane solution of n-butyllithium (6.20 ml, 9.92 mmol) in the atmosphere of argon, and the mixture was allowed to react for 30 min. To the solution was added 3.00 ml (40.9 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (25:1) yielded 1.07 g (3.28 mmol) of 1,6-bis[4-(α-hydroxyisopropyl)phenyl]-2,5-dioxahexane.

To 1.07 g (3.28 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 17 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (1:1) yielded 1.12 g (3.13 mmol) of 1,6-bis[4-(α-hydroxyisopropyl)phenyl]-2,5-dioxahexane.

NMR(ppm, CDCl$_3$)
8.10(s, 2 H), 7.52-7.14(m, 8 H), 4.53(s, 4 H),
3.62(s, 4 H), 1.55(s, 12 H).
IR($\nu$cm$^{-1}$, CHCl$_3$) 3520, 3330.

EXAMPLE 30

Bis[2-chloro-4-(α-hydroperoxyisopropyl)benzyl]ether

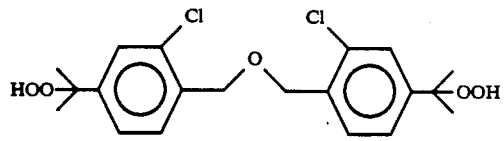

To a solution of 271 mg (6.78 mmol) of sodium hydride contained at 60% in mineral oil in dry dimethylformamide (25 ml) was added 1.00 g (4.52 mmol) of 4-bromo-2-chlorobenzyl alcohol in an atmosphere of argon, and the mixture was allowed to react at 40°-50° C. for 30 min. Then, 1.54 g (5.42 mmol) of 4-bromo-2-chlorobenzyl bromide was added, and the mixture was reacted at room temperature for 18 hours. To the reaction mixture at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with ethyl acetate-hexane (1:4) yielded 1.69 g (3.97 mmol) of bis(4-bromo-2-chlorobenzyl) ether.

To a solution of 1.69 g (3.97 mmol) of the above-obtained compound in dry tetrahydrofuran (50 ml) at −78° C. was added a 1.60M hexane solution of n-butyllithium (5.46 ml, 8.73 mmol) in the atmosphere of argon, and the mixture was allowed to react for 30 min. To the solution was added 4.00 ml (54.5 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 1.19 g (3.11 mmol) of bis[2-chloro-4-(α-hydroxyisopropyl)benzyl] ether.

To 1.19 g (3.11 mmol) of the above-obtained hydroxy compound were added 10 ml of ether, 30 ml of a 50% aqueous solution of hydrogen peroxide and 0.2 ml of concentrated sulfuric acid. The mixture was allowed to react at room temperature for 16 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (2:1) yielded 947 mg (2.28 mmol) of bis[2-chloro-4-(α-hydroperoxyisopropyl)benzyl] ether.

NMR (ppm, CDCl$_3$)
8.03(s, 2 H), 7.47-7.14(m, 6 H), 4.69(s, 4 H),
1.55(s, 12 H)
IR($\nu$cm$^{-1}$, CHCl$_3$) 3520, 3330

EXAMPLE 31

1,9-Bis[2-chloro-4-(α-hydroperoxyisopropyl)phenyl]-2,5,8-trioxanonane

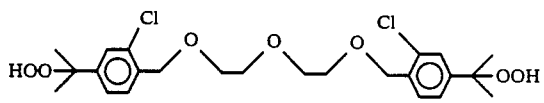

To a solution of 472 mg (11.8 mmol) of sodium hydride contained at 60% in mineral oil in dry dimethylformamide (50 ml) was added 500 mg (4.71 mmol) of diethylene glycol in an atmosphere of argon, and the mixture was allowed to react at 40°-50° C. for 30 min. Then, 2.96 g (10.4 mmol) of 4-bromo-2-chlorobenzyl bromide was added, and the mixture was reacted at room temperature for 16 hours. To the reaction solution at 0° C. was added a saturated aqueous solution of ammonium chloride followed by extraction with ethyl acetate. The organic layer was washed with water and then concentrated under reduced pressure. The residue thus obtained was subjected to silica gel column chromatography for separation and purification. Elution with ethyl acetatehexane (1:3) yielded 2.10 g (4.09 mmol) of 1,9-bis(4-bromo-2-chlorophenyl)-2,5,8-trioxanonane.

To a solution of 2.10 g (4.09 mmol) of the above-obtained compound in dry tetrahydrofuran (40 ml) at −78° C. was added a 1.60M hexane solution of n-butyllithium (5.63 ml, 9,00 mmol) in the atmosphere of argon, and the mixture was allowed to react for 30 min. To the solution was added 3.00 ml (40.9 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (50:1) yielded 1.44 g (3.06 mmol) of 1,9-bis[2-chloro-4-(α-hydroxyisopropyl)-phenyl]-2,5,8-trioxanonane.

To 1.44 g (3.06 mmol) of the above-obtained hydroxy compound were added 10 ml of ether, 30 ml of a 50% aqueous solution of hydrogen peroxide and 0.2 ml of concentrated sulfuric acid. The mixture was allowed to react at room temperature for 18 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (2:1) yielded 1.09 g (2.17 mmol) of 1,9-bis[2-chloro-4-(α-hydroperoxyisopropyl)phenyl]-2,5,8-trioxanonane.

NMR (ppm, CDCl$_3$)
7.98(s, 2 H), 7.45–7.16(m, 6 H), 4.64(s, 4 H),
3.62(s, 8 H), 1.53(s, 12 H).
IR($\nu$cm$^{-1}$, CHCl$_3$) 3530, 3330.

EXAMPLE 32

1,21-Bis[4-(α-hydroperoxyisopropyl)-2-methyl-phenyl]-2,5,8,11,14,17,20-heptaoxaheneicosane

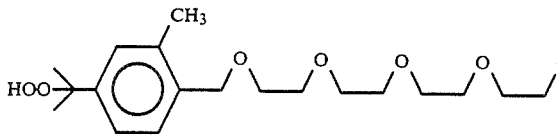

To a solution of 354 mg (3.85 mmol) of sodium hydride contained at 60% in mineral oil in dry dimethylformamide (20 ml) was added 1.00 g (3.54 mmol) of hexaethylene glycol, and the mixture was reacted at 40°–50° C. for 30 min. Then, 2.06 g (7.79 mmol) of 4-bromo-2-methylbenzyl bromide was added, and the mixture was allowed to react at room temperature for 17 hours. To the reaction solution at 0° C. was added a saturated aqueous solution of ammonium chloride followed by extraction with ethyl acetate. The organic layer was washed with water and concentrated under reduced pressure. The residue thus obtained was subjected to silica gel column chromatography for separation and purification. Elution with ethyl acetate-hexane (1:4) yielded 2.02 g (3.12 mmol) of 1,21-bis(4-bromo-2-methylphenyl)-2,5,8,11,14,17,20-heptaoxaheneicosane.

To a solution of 2.02 g (3.12 mmol) of the above-obtained compound in dry tetrahydrofuran (30 ml) at −78° C. was added a 1.60M hexane solution of n-butyllithium (4.29 ml, 6.86 mmol) in the atmosphere of argon, and the mixture was allowed to react for 30 min. To the solution was added 3.00 ml (40.9 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 1.37 g (2.25 mmol) of 1,21-bis[4-(α-hydroxyisopropyl)-2-methylphenyl]-2,5,8,11,14,17,20heptaoxaheneicosane.

To 1.37 g (2.25 mmol) of the above-obtained hydroxy compound were added 10 ml of ether, 30 ml of a 50% aqueous solution of hydrogen peroxide and 0.2 ml of concentrated sulfuric acid. The mixture was allowed to react at room temperature for 18 hours followed by addition of water and extraction with ethyl acetate. The organic layer was washed with water and then concentrated under reduce pressure. The residue thus obtained was subjected to silica gel column chromatography for separation and purification. Elution with ethyl acetate-hexane (2:1) yielded 1.07 g (1.67 mmol) of 1,21-bis[4-(α-hydroperoxyisopropyl)-2-methylphenyl]-2,5,8,11,14,17,20-heptaoxaheneicosane.

NMR (ppm, CDCl$_3$)
8.07(s, 2 H), 7.42–7.03(m, 6 H), 4.53(s, 4 H),
3 61(s, 24 H), 2.24(s, 6 H), 1.56(s, 12 H).
IR($\nu$cm$^{-1}$, CHCl$_3$) 3530, 3340.

EXAMPLE 33

N,N Bis[4-(α-hydroperoxyisopropyl)benzenesulfonyl]-piperazine

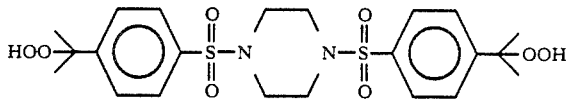

To a solution of 0.79 g (9.16 mmol) of piperazine in dry pyridine (20 ml) was added 5.15 g (20.15 mmol) of 4-bromobenzenesulfonyl chloride in an atmosphere of argon, and the mixture was allowed to react at 0° C. for 3 hours. To the solution was added water followed by extraction with ethyl acetate. The organic layer was washed with water and then concentrated under reduced pressure. The residue thus obtained was subjected to silica gel column chromatography for separation and purification. Elution with dichloromethane yielded 4.37 g (8.34 mmol) of N,N'-bis(4-bromobenzenesulfonyl)piperazine.

To a solution of 4.37 g (8.34 mmol) of the above-obtained compound in dry tetrahydrofuran (20 ml) at −78° C. was added a 1.60M hexane solution of n-butyllithium (11.5 ml, 18.35 mmol) in the atmosphere of argon, and the mixture was allowed to react for 30 min. To the solution was added 10.0 ml (136 mmol) of acetone, and the mixture was reacted at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol yielded 2.72 g (6.42 mmol) of N,N'-bis[4-(α-hydroxyisopropyl)benzenesulfonyl]piperazine.

To 2.72 g (6.42 mmol) of the above-obtained hydroxy compound were added 15 ml of ether, 20 ml of a 30% aqueous solution of hydrogen peroxide and 0.50 ml of concentrated sulfuric acid. The mixture was allowed to react at room temperature for 17 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (2:1) yielded 2.22 g (4.87 mmol) of N,N'-bis[4-(α-hydroperoxyisopropyl)benzenesulfonyl]-piperazine.

NMR (ppm, CDCl$_3$)
7.83(s, 2 H), 7.67–7.16(m, 8 H), 2.82(s, 8 H), 1.61(s, 12 H).
IR($\nu$cm$^{-1}$, CHCl$_3$) 3530, 3330.

EXAMPLE 34

1,3-Bis[4-(α-hydroperoxyisopropyl)benzyl]sulfone

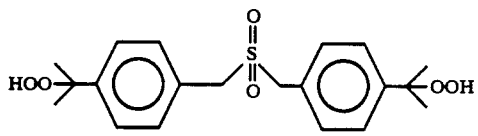

To a solution of 1.85 g (9.11 mmol) of 4-bromobenzylmercaptan in dry dichloromethane (30 ml) were added 2.72 g (10.9 mmol) of 4-bromobenzyl bromide and 2.31 g (22.8 mmol) of triethylamine in an atmosphere of argon, and the mixture was allowed to react at room temperature for 16 hours. To the solution was added water followed by extraction with ethyl acetate. The organic layer was washed with water and then concentrated under reduced pressure. The residue thus obtained was subjected to silica gel column chromatography for separation and purification. Elution with ethyl acetate-hexane (1:4) yielded 3.08 g (8.29 mmol) of bis(4-bromobenzyl)sulfide.

To a solution of 3.08 g (8.29 mmol) of said compound in dry tetrahydrofuran (50 ml) at −78° C. was added a 1.60M hexane solution of n-butyllithium (11.4 ml, 18.2 mmol), and the mixture was allowed to react for 30 min. To the solution was added 4.0 ml (54.5 mmol) of acetone, and the mixture was allowed to react at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with dichloromethane-methanol (100:1) yielded 1.97 g (5.97 mmol) of bis[4-(α-hydroxyisopropyl)benzyl]sulfide.

To 1.97 g (5.97 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 20 hours followed by addition of water and extraction with ethyl acetate. The organic layer was washed with water and then concentrated under reduced pressure. The residue thus obtained was subjected to silica gel column chromatography for separation and purification. Elution with ethyl acetate-hexane (3:1) yielded 1.58 g (4.36 mmol) of bis[4-(α-hydroperoxyisopropyl)benzyl]sulfone.

NMR (ppm, DMSO-d$_6$)
7.49(s, 8 H), 4.62(s, 4 H), 1.49(s, 12 H).
IR ($\nu$cm$^{-1}$, KBr) 3400.

EXAMPLE 35

2-[2-[α-[4-(α-hydroperoxyisopropyl)toluene]sulfonyl]-ethanesulfonyl]ethanesulfonylmethyl-4-(α-hydroperoxyisopropyl)benzene

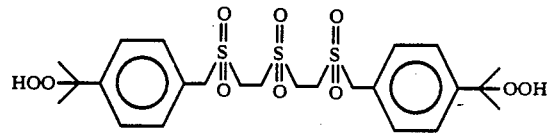

To a solution of 5.00 g (20.0 mmol) of 4-bromobenzyl bromide in dry tetrahydrofuran (24 ml) was added 1.30 ml (9.97 mmol) of 2-marcaptoethyl sulfide in an atmosphere of argon, and the mixture was allowed to react at 0° C. for 6 hours. To the solution was added water followed by extraction with benzene. The organic layer was washed with water and then concentrated under reduced pressure. The residue thus obtained was subjected to silica gel column chromatography for separation and purification. Elution with dichloromethane-hexane (1:5) yielded 4.46 g (9.69 mmol) of 1,9-bis(4-bromobenzene)-2,5,8-trithianonane.

To a solution of 4.46 g (9.68 mmol) of the above-obtained compound in 30 ml of dry tetrahydrofuran at −78° C. was added a 1.60M hexane solution of n-butyllithium (18.8 ml, 30.0 mmol) in the atmosphere of argon, and the mixture was allowed to react for 30 min. To the solution was added 10.0 ml (136 mmol) of acetone, and the mixture was allowed to react at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography. Elution with dichloromethane yielded 3.36 g (7.45 mmol) of 1,9-bis[4-(α-hydroxyisopropyl)phenyl]-2,5,8-trithianonane.

To 3.36 g (7.45 mmol) of the above-obtained hydroxy compound were added 20 ml of ether, 20 ml of a 30% aqueous solution of hydrogen peroxide and 0.50 ml of concentrated sulfuric acid. The mixture was allowed to react at room temperature for 19 hours followed by addition of water and extraction with ethyl acetate. The organic layer was washed with water and then concentrated under reduced pressure. There was obtained 3.15 g (5.44 mmol) of 2-[2-[α-[4-(α-hydroperoxyisopropyl)-toluene]sulfonyl]ethanesulfonyl]-ethanesulfonylmethyl-4-(α-hydroperoxyisopropyl)benzene.

NMR (ppm, DMSO-d$_6$)
7.38(s, 8 H), 4.57(s, 4 H), 3.62(s, 8 H), 1.45(s, 12 H).
IR ($\nu$cm$^{-1}$, KBr) 3400.

EXAMPLE 36

N,N'-Bis[4-(α-hydroperoxyisopropyl)benzenesulfonyl]-N,N'-dimethyl-3,6,9-trioxaundecane-11-diamine

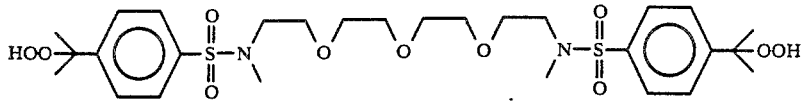

To a solution of 1.64 g (8.44 mmol) of tetraethylene glycol in dry pyridine (30 ml) was added 3.55 g (18.6 mmol) of p-toluenesulfonyl chloride in an atmosphere of argon, and the mixture was allowed to react at room temperature for 15 hours. To the solution was added water followed by addition of conc. hydrochloric acid to adjust the pH to 4, and the resulting mixture was extracted with ethyl acetate. The organic layer was washed with water and then concentrated under reduced pressure. The residue thus obtained was subjected to silica gel column chromatography for separation and purification. Elution with dichloromethane-methanol (100:1) yielded 3.78 g (7.52 mmol) of O,O'-ditosyl-3,6,9-trioxaundecane-1,11-diol.

To a solution of 9.38 g (36.7 mmol) of p-toluenesulfonyl chloride in dry pyridine was added 12.4 g (184 mmol) of methylamine hydrochloride in the atmosphere of argon, and the mixture was allowed to react at room temperature for 4 hours. To the solution was added water followed by extraction with ethyl acetate. The organic layer was washed with water and then concentrated under reduced pressure. The residue thus obtained was subjected to silica gel column chromatography for separation and purification. Elution with dichloromethane yielded 8.46 g (33.8 mmol) of 4-bromobenzenesulfonyl N-methylamide.

To a solution of 1.56 g (39.1 mmol) of sodium hydride contained at 60% in mineral oil in dry dimethylformamide (50 ml) was added 4.70 g (18.8 mmol) of 4-bromobenzenesulfonyl-N-methylamide in the atmosphere of argon, and the mixture was allowed to react at room temperature for 30 min. Then, 3.78 g (7.52 mmol) of O,O'-tosyl-3,6,9-trioxaundecane-1,11-diol was added, and the mixture was allowed to react for 18 hours. The solution was added to ice water followed by extraction with ethyl acetate. The organic layer was washed with water and then concentrated under reduced pressure. The residue thus obtained was subjected to silica gel column chromatography for separation and purification. Elution with dichloromethane yielded 4.66 g (7.07 mmol) of N,N'-(4-bromobenzenesulfonyl)-N,N'-dimethyl-3,6,9-trioxaundecane-1,11-diamine.

To a solution of 4.66 g (7.07 mmol) of the above-obtained compound in dry tetrahydrofuran (50 ml) at −78° C. was added a 1.60M hexane solution of n-butyllithium (9.8 ml, 15.6 mmol) in the atmosphere of argon, and the mixture was allowed to react for 30 min. To the solution was added 4.0 ml (54.5 mmol) of acetone, and the mixture was allowed to react at −78° C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with ethyl acetatehexane (1:4) yielded 3.18 g (5.16 mmol) of N,N'-[4-(α-hydroxyisopropyl)benzenesulfonyl]-N,N'-dimethyl-3,6,9-trioxaundecane-1,11-diamine.

To 3.18 g (5.16 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 17 hours followed by addition of water and extraction with ethyl acetate. The organic layer was washed with water and then concentrated under reduced pressure. The residue thus obtained was subjected to silica gel column chromatography for separation and purification. Elution with dichloromethane-methanol (50:1) yielded 2.54 g (3.92 mmol) of N,N'-[4-(α-hydroperoxyisopropyl)-benzenesulfonyl]-N,N'-dimethyl-5,6,9-trioxaundecane-1,11 diamine.

NMR (ppm, CDCl$_3$)
7.82(s, 2 H), 7.60(s, 8 H), 3.57(t, 4H, J=5 Hz),
3.53(s, 8 H), 3.18(t, 4H, J=5 Hz), 2.81(s, 6 H),
1.62(s, 12 H).
IR ($\nu$cm$^{-1}$,CHCl$_3$) 3532, 3330.

EXAMPLE 37

N,N'-Bis[4-(α-hydroperoxyisopropyl)benzenesulfonyl]-N,N'-dimethyl-3,6,9,12,15-pentaoxaheptadecane-1,17-diamine

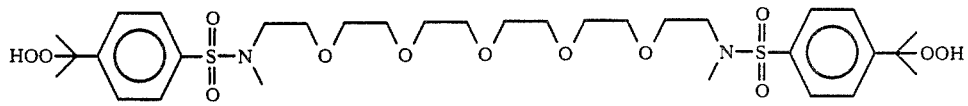

To a solution of 1.48 g (5.24 mmol) of hexaethylene glycol in dry pyridine (30 ml) was added 2.19 g (11.5 mmol) of p-toluenesulfonyl chloride in an atmosphere of argon, and the mixture was allowed to react at room temperature for 15 hours. To the solution was added water followed by addition of conc. hydrochloric acid to adjust the pH to 4, and the resulting mixture was extracted with ethyl acetate. The organic layer was washed with water and then concentrated under reduced pressure. The residue thus obtained was subjected to silica gel column chromatography for separation and purification. Elution with dichloromethane-methanol (100:1) yielded 2.85 g (4.82 mmol) of O,O'-ditosyl-3,6,9,12,15-pentaoxaheptadecane-1,17-diol.

To a solution of 3.14 g (12.3 mmol) of 4-bromobenzenesulfonyl chloride in dry pyridine was added 4.15 g (61.5 mmol) of methylamine hydrochloride in the atmosphere of argon, and the mixture was allowed to react at room temperature for 4 hours. To the solution was added water followed by extraction with ethyl acetate. The organic layer was washed with water and then concentrated under reduced pressure. The residue was subjected to silica gel column chromatography for separation and purification. Elution with dichloromethane yielded 2.69 g (11.6 mmol) of 4-bromobenzenesulfonyl-N-methylamide.

To a solution of 1.02 g (25.5 mmol) of sodium hydride contained at 60% in mineral oil in dry dimethylformamide (50 ml) was added 2.96 g (11.6 mmol) of 4-bromobenzenesulfonyl-N-methylamide in the atmosphere of argon, and the mixture was allowed to react at room temperature for 30 min. Then, 2.85 g (4.82 mmol) of O,O'-ditosyl- 3,6,9,12,15-pentaoxaheptadecane-1,17-diol, and the resulting mixture was allowed to react for 22 hours. The solution was added to ice water followed by extraction with ethyl acetate. The organic layer was washed with water and then concentrated under reduced pressure. The residue obtained was subjected to silica gel column chromatography for separation and purification. Elution with dichloromethane yielded 3.28 g (4.39 mmol) of N,N'-bis(4-bromobenzenesulfonyl)-N,N'-dimethyl-3,6,9,12,15-pentaoxaheptadecane-1,17-diamine.

To a solution of 3.28 g (4.39 mmol) of the above-obtained compound in dry tetrahydrofuran (50 ml) at $-78°$ C. was added a 1.60M hexane solution of n-butyl-lithium (6.0 ml, 9.66 mmol) in the atmosphere of argon, and the mixture was allowed to react for 30 min. To the solution was added 4.0 ml (54.5 mmol) of acetone, and the mixture was allowed to react at $-78°$ C. for 10 min. followed by addition of a saturated aqueous solution of ammonium chloride and extraction with ethyl acetate. The organic layer was washed with water and then concentrated under reduced pressure. The residue thus obtained was subjected to silica gel column chromatography for separation and purification. Elution with ethyl acetatehexane (1:4) yielded 2.35 g (3.34 mmol) of N,N'-bis[4-($\alpha$-hydroxyisopropyl)benzenesulfonyl]-N,N'-dimethyl-3,6,9,12,15-pentaoxaheptadecane-1,17-diamine.

To 2.35 g (3.34 mmol) of the above-obtained hydroxy compound were added 10 ml of ether, 20 ml of a 30% aqueous solution of hydrogen peroxide and 0.50 ml of concentrated sulfuric acid. The mixture was allowed to react at room temperature for 17 hours followed by addition of water and extraction with ethyl acetate. The organic layer was washed with water and then concentrated under reduced pressure. The residue thus obtained was subjected to silica gel column chromatography for separation and purification. Elution with dichloromethane-methanol (50:1) yielded 1.89 g (2.57 mmol) of N,N'-bis[4-($\alpha$-hydroperoxyisopropyl)benzenesulfonyl]-N,N'-dimethyl-3,6,9,12,15-pentaoxaheptadecane-1,17diamine.

NMR (ppm, $CDCl_3$)
7.86(s, 2 H), 7.53(s, 8 H), 3.54(t, 4H, J=5 Hz), 3.52(s, 16 H), 3.09(t, 4H, J=5 Hz), 2.90(s, 6 H), 1.65(s, 12 H).
IR ($\nu cm^{-1}$, $CHCl_3$) 3530, 3340.

EXAMPLE 38

| Preparative method of test paper | |
|---|---|
| Solution I | |
| $\alpha$-Hydroperoxyisopropylphenyl compound (I) or (II) | |
| Molecular weight $\times \frac{4.48}{m} \times 10^{-3}$ g | |
| (m is number of the hydroperoxy group contained in one molecule) | |
| p-Toluenesulfonyl-N-diethylamide | 5.0 g |
| Sodium dioctylsulfosuccinate | 1.5 g |
| Ethanol | 100 ml |

A filter paper is thoroughly made wet with Solution I and dried in a drying oven at 40° C. for 20 min.

| Solution II | |
|---|---|
| Acrylamide | 10 g |
| Polyethylene glycol | 10 g |
| Trisodium citrate dihydrate | 9 g |
| Citric acid monohydrate | 1 g |
| Saponin | 100 mg |
| EDTA-2Na | 30 mg |
| Water | 100 ml |

The filter paper treated with Solution I and dried is thoroughly made wet with Solution II and dried in a drying oven at 40° C. for 50 min.

| Solution III | |
|---|---|
| Orthotolidine | 1.20 g |
| 3-Aminoquinoline | 0.5 g |
| Benzene | 100 ml |

The filter paper treated with Solution II and dried is thoroughly made wet with Solution III and dried in a drying oven at 40° C. for 10 min. This is used as a test paper for evaluation.

TEST EXAMPLE 1

The test paper prepared as described in the preparative example is soaked in a specimen for one second. Referring to a selected color tone table, color development of the above-mentioned test paper is read by naked eyes in terms of the judgement code indicated in the color tone table. On the basis of the degree of color development according to said color tone table, concentration of the occult blood in the specimen is judged. Correlations between the judgement code and the hemoglobin concentration are shown below.

TABLE 1

| Judgement code | Hemoglobin concentration |
|---|---|
| 3+ | 250/$\mu$l |
| 2+ | 50/$\mu$l |
| + | 10/$\mu$l |

It is noted that the color tone correlated to the hemoglobin concentration in the color tone table indicates color of the test piece prepared by the method described in the preparative example using a peroxide, 2,5-dimethylhexane-2,5-dihydroperoxide judged after 60 seconds.

As a result, 4-($\alpha$-hydroperoxyisopropyl)benzyl benzyl ether and 4-(2,4,7-trioxaoctyl)cumene hydroperoxide and bis[4-($\alpha$-hydroperoxyisopropyl)benzyl] ether developed the color corresponding to the color tone table judged after approximately 10 seconds, whereas N,N-dimethyl-[4-($\alpha$-hydroperoxyisopropyl)benzene]-sulfoamide after approximately 20 seconds. On the other hand, it required approximately 25 seconds for the test paper with cumene hydroperoxide to develop the color corresponding to the color tone table. Note that it requires 60 seconds for 2,5-dimethylhexane-2,5-dihydroperoxide used for the preparation of the color tone table.

The above findings indicated that the $\alpha$-hydroperoxyisopropylphenyl compound (I) or (II) is more highly sensitive than 2,5-dimethylhexane-2,5-dihydroperoxide or cumene hydroperoxide, which is used in commercially available test papers for the measurement of occult blood in urine.

Next, results of the judgement in the test conducted after storage of 2 weeks or 4 weeks at 60° C. are shown in Table 2.

TABLE 2

| Test compound | Hemoglobin concentration Storage condition | | | |
|---|---|---|---|---|
| | 60° C., 2 weeks | | 60° C., 4 weeks | |
| | Time for judgement | | | |
| | 30 seconds | 60 seconds | 30 seconds | 60 seconds |
| A | +~2+ | 2+ | + | +~2+ |
| B | 2+ | 2+~3+ | +~2+ | 2+ |
| C | 2+ | 2+~3+ | +~2+ | 2+ |
| D | +~2+ | 2+ | 0~+ | + |
| E | 0 | 0 | 0 | 0 |
| F | + | +~2+ | 0 | 0 |
| G | 0~+ | + | 0 | 0 |

Note
The indications 0~+, +~2+ and 2+~3+ indicate a color tone ranged between the numbers indicated. The indication 0~⊕ indicates a middle color tone nearer to +.

TEST COMPOUND

A: 4(2,4,7-Trioxaoctyl)cumene hydroperoxide
B: 4-(α-Hydroperoxyisopropyl)benzyl benzyl ether
C: Bis[4-(α-hydroperoxyisopropyl)benzyl]benzyl ether
D: N,N-Dimethyl-[4-(α-hydroperoxyisopropyl)benzene]-sulfoamide
E: Cumene hydroperoxide (Control)
F: 4-Octylcumene hydroperoxide (Control)
G: 2,5-Dimethylhexane-2,5-dihydroperoxide (Control)

It is seen from Table 2 that 4-(α-hydroperoxyisopropyl)benzyl benzyl ether, 4-(2,4,7-trioxaoctyl)cumene hydroperoxide, bis[4-(α-hydroperoxyisopropyl)benzyl]ether and N,N-dimethyl-]4-(α-hydroperoxyisopropyl)benzene]sulfoamide of the invention are superior in stability with elapse of time. Particularly, comparison between 4-(2,4,7-trioxaoctyl)cumene hydroperoxide and 4-octylcumene hydroperoxide reveals usefulness of the ether bond.

TEST EXAMPLE 2

There is contained vitamin C in human urine owing to drinking water, vitamin preparations, etc. Test paper for the measurement of occult blood in urine undergoes pseudonegative reaction due to the presence of vitamin C. A performance test was carried out with the α-hydroperoxyisopropylphenyl compound (I) or (II) using the test piece prepared by the method shown in the preparative example in the presence of vitamin C at a concentration of 20 mg/dl or 100 mg/dl. Results are shown in Table 3 and Table 4.

TABLE 3

| | Vitamin C concentration in urine at 20 mg/dl | | | | | | | | |
|---|---|---|---|---|---|---|---|---|---|
| | Hemoglobin concentration | | | | | | | | |
| | 10/μl + | | | 50/μl 2+ | | | 250/μl 3+ | | |
| | Time for judgement (sec.) | | | | | | | | |
| | 10 | 30 | 60 (sec.) | 10 | 30 | 60 (sec.) | 10 | 30 | 60 (sec.) |
| A | 0~⊕ | 0~⊕ | 0 | 2+ | 2+ | 2+ | 3+ | 3+< | 3+< |
| B | + | 0~⊕ | 0 | 2+~3+ | 2+~3+ | 2+~3+ | 3+ | 3+< | 3+< |
| C | + | 0~⊕ | 0 | 2+~3+ | 2+~3+ | 2+~3+ | 3+ | 3+< | 3+< |
| E | 0~⊕ | 0~+ | 0 | +~2+ | 2+ | 2+ | 3+ | 3+< | 3+< |
| F | 0 | 0 | 0 | + | + | + | 2+ | 2+ | 2+ |
| G | 0 | 0 | 0 | + | +~2+ | 2+ | 2+ | 3+ | 3+ |

TABLE 4

| | Vitamin C concentration in urine at 100 mg/dl | | | | | | | | |
|---|---|---|---|---|---|---|---|---|---|
| | Hemoglobin concentration | | | | | | | | |
| | 10/μl + | | | 50/μl 2+ | | | 250/μl 3+ | | |
| | Time for judgement (sec.) | | | | | | | | |
| | 10 | 30 | 60 (sec.) | 10 | 30 | 60 (sec.) | 10 | 30 | 60 (sec.) |
| A | 0 | 0 | 0 | +~2+ | + | 0 | 3+ | 3+ | 3+ |
| B | 0 | 0 | 0 | 2+ | +~2+ | 0~⊕ | 3+ | 3+ | 3+ |
| C | 0 | 0 | 0 | 2+ | +~2+ | 0~⊕ | 3+ | 3+ | 3+ |
| E | 0 | 0 | 0 | +~2+ | + | 0 | 3+ | 3+ | 3+ |
| F | 0 | 0 | 0 | + | 0~+ | 0 | 2+ | 2+ | 2+ |
| G | 0 | 0 | 0 | 0~+ | 0~+ | 0 | 2+ | 3+ | 2+~3+ |

It is seen from the results in Tables 3 and 4 that the peroxides of the invention, 4-(α-hydroperoxyisopropyl)benzyl benzyl ether and 4-(2,4,7-trioxaoctyl)cumene hydroperoxide and bis[4-(α-hydroperoxyisopropyl)benzyl]ether had a vitamin C-inhibitory effect equal to or more than that of cumene hydroperoxide, and also that comparison between 4-(2,4,7-trioxaoctyl)cumene hydroperoxide and 4-octylcumene hydroperoxide reveals effectiveness of the side chain containing the ether bond.

TEST EXAMPLE 3

It is known that when the test piece for the measurement of occult blood and the test piece for the measurement of glucose are adjacent each other on a stick, discoloration is produced in the test paper for the measurement of glucose.

Test pieces prepared according to the above preparative example using as the peroxide 4-(α-hydroperoxyisopropyl)benzyl benzyl ether, 4-(2,4,7-trioxaoctyl)cumene hydroperoxide, bis[4-(α-hydroperoxyisopropyl)benzyl] ether and N,N-dimethyl-[4-(α-hydroperoxyisopropyl)benzenesulfoamide, and a test piece using 2,5-dimethylhexane-2,5-dihydroperoxide respectively were placed on a separate stick. A test piece for glucose was placed at the adjacent site on each of the sticks which were stored at 40° C. for one month. Whereas the former did not produce discoloration on the glucose test piece, the latter produced discoloration. This indicates that the peroxides of the invention produce little influence upon the other adjacent test item.

Industrial Applicability

The α-hydroperoxyisopropylphenyl compounds (I) or (II) are effectively used for detecting peroxide-active substances, particularly blood or hemoglobin. As a matter of fact, when the α-hydroperoxyisopropylphenyl compound (I) or (II) of the invention is used as an organic hydroperoxide in peroxide-active substance-testing compositions or test devices consisting of an organic hydroperoxide and a color-developing indicator, there are provided test compositions and test devices having the following characteristics:

(1) Being stable with elapse of time and capable of maintaining good sensitivity even if stored for a long period of time.

(2) In case of multi-item test pieces for detecting components of urine, producing no discoloration on other adjacent test pieces such as that for glucose with no reduction of the performance associated.

(3) Being faster in the color-developing reaction and higher in the sensitivity for color development than prior-art test compositions.

Therefore, the present invention is utilized in a field of medical instrument industry.

What is claimed is:

1. An α-hydroxyperoxyisopropylphenyl compound having the general formula

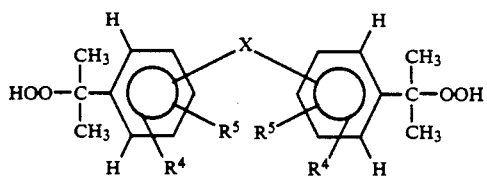

wherein X represents a straight- or branched-chain alkylene group which may contain an ether bond in the chain or a divalent organic group containing sulfur atom and $R^4$ and $R^5$ are the same or different and respectively represent hydrogen atom, a lower alkyl group, a halogen atom, carboxyl group or nitro group.

2. A compound of the general formula according to claim 1, wherein the alkylene group in X is a group having 2-100 carbon atoms.

3. A compound of the general formula according to claim 1 wherein the alkylene group in X is an alkylene group represented by the formula given below.

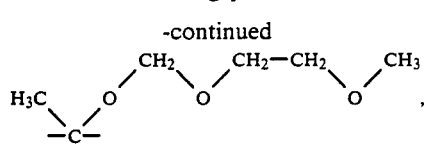

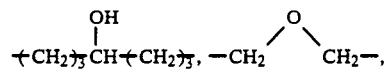

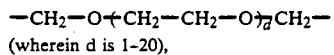
(wherein d is 1-20),

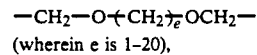
(wherein e is 1-20),

or

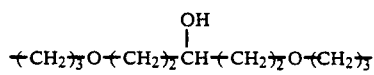

4. A process for preparing α-hydroperoxyisopropylphenyl compounds having the general formula according to claim 1 which comprises oxidizing with an aqueous solution of hydrogen peroxide of α-hydroxyisopropylphenyl compound having the general formula

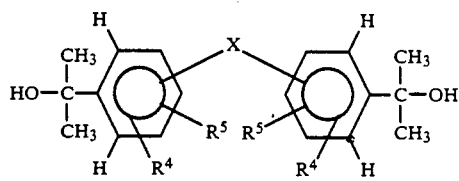

wherein $R^4$-$R^5$ and X respectively have the same meanings as defined in claim 1.

5. A test composition for the measurement of peroxide-active substances comprising an α-hydroperoxyisopropylphenyl compound having the general formula according to claim 1 and an oxidation coloration indicator.

6. A composition according to claim 5 wherein the oxidation coloration indicator is orthotolidine, benzidine or leucomalachite green.

7. A test device for the measurement of peroxide-active substances comprising a carrier on which a composition containing an α-hydroperoxyisopropylphenyl compound having the general formula according to claim 1 and an oxidation coloration indicator is carried.

8. A test device according to claim 7 wherein the carrier is non-woven cloth made of filter paper, glass fibers or a plastic material.

9. A compound of the formula according to item 1 wherein the organic groups $R^4$ and $R^5$ are hydrogen or a lower alkyl, and the alkylene group in X is a group having 2-100 carbon atoms and containing an ether bond.

* * * * *